United States Patent
Wei et al.

(10) Patent No.: US 10,588,838 B2
(45) Date of Patent: *Mar. 17, 2020

(54) COMPOSITIONS FOR TREATING SKIN

(71) Applicant: The Procter & Gamble Company, Cincinnati, OH (US)

(72) Inventors: Karl Shiqing Wei, Mason, OH (US); Edward Dewey Smith, III, Mason, OH (US); Shawn Lynn Mansfield, Liberty Township, OH (US); Peter Herbert Koenig, Montgomery, OH (US); Wei Ji, Cincinnati, OH (US); Yogesh Suradkar, Bangalore (IN); Deepa Bagchi, Singapore (SG); Sujatha Logou, Singapore (SG); Stevan David Jones, Hyde Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/270,861

(22) Filed: Feb. 8, 2019

(65) Prior Publication Data
US 2019/0167550 A1    Jun. 6, 2019

Related U.S. Application Data

(63) Continuation of application No. 15/669,001, filed on Aug. 4, 2017, now abandoned, which is a (Continued)

(51) Int. Cl.
*C11D 1/29* (2006.01)
*C11D 1/88* (2006.01)
(Continued)

(52) U.S. Cl.
CPC .............. *A61K 8/39* (2013.01); *A61K 8/0258* (2013.01); *A61K 8/0295* (2013.01); *A61K 8/19* (2013.01);
(Continued)

(58) Field of Classification Search
CPC .... C11D 1/29; C11D 1/88; C11D 1/94; C11D 3/046; C11D 3/122; C11D 3/37;
(Continued)

(56) References Cited

U.S. PATENT DOCUMENTS 2,438,091 A    3/1948 Lynch
2,528,378 A    10/1950 Mannheimer et al.
(Continued)

FOREIGN PATENT DOCUMENTS

DE    10 2008 035 172 A1    2/2010
EP    1 383 542 B1    4/2008
(Continued)

OTHER PUBLICATIONS

International Search Report PCT/US2011/039907 including Written Opinion, dated Feb. 12, 2012, 13 pages.

*Primary Examiner* — Brian P Mruk

(57) ABSTRACT

A personal care composition comprising: at least a first phase and a second phase wherein said first phase comprises a) an aqueous structured surfactant phase comprising STnS where n is between about 0 and about 2.5; b) c) a structuring system comprising i. optionally, a non-ionic emulsifier; ii. optionally, from about 0.05% to about 5%, by weight of said personal care composition, of an associative polymer; iii. an electrolyte; and said second phase comprises a) a benefit phase comprising from 1% to about 50%, by weight of said personal care composition, of a hydrophobic benefit agent.

20 Claims, 10 Drawing Sheets

Related U.S. Application Data continuation of application No. 13/157,665, filed on Jun. 10, 2011, now Pat. No. 9,750,674.

(60) Provisional application No. 61/354,118, filed on Jun. 11, 2010.

(51) Int. Cl.

| | | |
|---|---|---|
| *C11D 1/94* | (2006.01) | |
| *C11D 3/37* | (2006.01) | |
| *A61K 8/06* | (2006.01) | |
| *A61K 8/19* | (2006.01) | |
| *A61K 8/31* | (2006.01) | |
| *A61K 8/39* | (2006.01) | |
| *A61K 8/46* | (2006.01) | |
| *A61K 8/81* | (2006.01) | |
| *A61K 8/891* | (2006.01) | |
| *A61K 8/92* | (2006.01) | |
| *A61K 8/97* | (2017.01) | |
| *A61Q 19/00* | (2006.01) | |
| *A61Q 19/10* | (2006.01) | |
| *A61K 8/02* | (2006.01) | |
| *A61K 8/41* | (2006.01) | |
| *A61K 8/44* | (2006.01) | |

(52) U.S. Cl.
CPC .............. *A61K 8/31* (2013.01); *A61K 8/416* (2013.01); *A61K 8/44* (2013.01); *A61K 8/447* (2013.01); *A61K 8/463* (2013.01); *A61K 8/8152* (2013.01); *A61K 8/922* (2013.01); *A61Q 19/10* (2013.01); *A61K 2800/596* (2013.01)

(58) Field of Classification Search
CPC ... A61K 8/06; A61K 8/19; A61K 8/31; A61K 8/39; A61K 8/46; A61K 8/81; A61K 8/891; A61K 8/92; A61K 8/97; A61Q 19/00; A61Q 19/10
See application file for complete search history.

(56) References Cited

U.S. PATENT DOCUMENTS

| | | | |
|---|---|---|---|
| 2,658,072 | A | 11/1953 | Kosmin |
| 3,915,921 | A | 10/1975 | Schlatzer, Jr. |
| 3,940,351 | A | 2/1976 | Schlatzer, Jr. |
| 4,062,817 | A | 12/1977 | Westerman |
| 4,429,097 | A | 1/1984 | Chang et al. |
| 5,011,681 | A | 4/1991 | Ciotti et al. |
| 5,147,576 | A | 9/1992 | Montague et al. |
| 5,364,617 | A | 11/1994 | Bush et al. |
| 5,462,963 | A | 10/1995 | Bush et al. |
| 5,487,884 | A | 1/1996 | Bissett et al. |
| 5,652,228 | A | 7/1997 | Bissett |
| 5,681,852 | A | 10/1997 | Bissett |
| 5,965,502 | A | 10/1999 | Balzer |
| 6,068,834 | A | 5/2000 | Kvalnes et al. |
| 6,150,312 | A | 11/2000 | Puvvada et al. |
| 6,217,888 | B1 | 4/2001 | Oblong et al. |
| 6,395,691 | B1 | 5/2002 | Tsaur |
| 6,433,061 | B1 | 8/2002 | Marchant et al. |
| 6,537,527 | B1 | 3/2003 | Kvalnes et al. |
| 6,635,702 | B1 | 10/2003 | Schmucker-Castner et al. |
| 6,645,511 | B2 | 11/2003 | Aronson et al. |
| 6,759,376 | B2 | 7/2004 | Zhang et al. |
| 6,780,826 | B2 | 8/2004 | Zhang et al. |
| 6,897,253 | B2 | 5/2005 | Schmucker-Castner et al. |
| 7,084,104 | B2 | 8/2006 | Martin et al. |
| 7,098,180 | B2 | 8/2006 | Ganopolsky et al. |
| 7,119,059 | B2 | 10/2006 | Librizzi et al. |
| 7,157,414 | B2 | 1/2007 | Librizzi et al. |
| 7,488,707 | B2 | 2/2009 | Frantz et al. |
| 7,511,003 | B2 | 3/2009 | Focht et al. |
| 7,527,077 | B2 | 5/2009 | McCall et al. |
| 7,531,497 | B2 | 5/2009 | Midha et al. |
| 7,649,047 | B2 | 1/2010 | Tamareselvy et al. |
| 7,666,825 | B2 | 2/2010 | Wagner et al. |
| 7,754,666 | B2 | 7/2010 | Walters et al. |
| 7,763,419 | B2 | 7/2010 | Hendrix et al. |
| 7,767,389 | B2 | 8/2010 | Hendrix et al. |
| 7,771,924 | B2 | 8/2010 | Hendrix et al. |
| 7,771,925 | B2 | 8/2010 | Hendrix et al. |
| 8,067,517 | B2 | 11/2011 | Yoshinaka et al. |
| 8,105,996 | B2 | 1/2012 | Wei et al. |
| 8,309,667 | B2 | 11/2012 | Yoshinaka et al. |
| 9,717,674 | B1 * | 8/2017 | Guskey ............... A61K 8/8164 |
| 9,750,674 | B2 * | 9/2017 | Wei ..................... A61K 8/0258 |
| 2004/0092415 | A1 | 5/2004 | Focht et al. |
| 2004/0223929 | A1 | 11/2004 | Clapp et al. |
| 2004/0223991 | A1 | 11/2004 | Wei et al. |
| 2004/0235702 | A1 | 11/2004 | Hawkins |
| 2005/0019299 | A1 | 1/2005 | Librizzi et al. |
| 2005/0020468 | A1 | 1/2005 | Frantz et al. |
| 2005/0049172 | A1 | 3/2005 | Lukenbach et al. |
| 2005/0075256 | A1 | 4/2005 | Librizzi et al. |
| 2005/0100570 | A1 | 5/2005 | Wei et al. |
| 2005/0276768 | A1 | 12/2005 | Wei et al. |
| 2006/0040834 | A1 | 2/2006 | Hilliard et al. |
| 2006/0079419 | A1 | 4/2006 | Wagner et al. |
| 2006/0079420 | A1 | 4/2006 | Wagner et al. |
| 2006/0079421 | A1 | 4/2006 | Wagner et al. |
| 2006/0182699 | A1 | 8/2006 | Taylor et al. |
| 2006/0189495 | A1 | 8/2006 | Librizzi et al. |
| 2007/0155637 | A1 | 7/2007 | Smith et al. |
| 2007/0196344 | A1 | 8/2007 | Osborne et al. |
| 2007/0224696 | A1 | 9/2007 | Honkonen et al. |
| 2007/0286832 | A1 | 12/2007 | Clapp et al. |
| 2008/0095733 | A1 | 4/2008 | Griffin et al. |
| 2008/0112913 | A1 | 5/2008 | Librizzi et al. |
| 2008/0233061 | A1 * | 9/2008 | Gates ..................... A01N 25/30 424/59 |
| 2008/0242573 | A1 | 10/2008 | Wei |
| 2009/0005449 | A1 | 1/2009 | Gunn et al. |
| 2009/0005460 | A1 | 1/2009 | Gunn et al. |
| 2009/0311348 | A1 | 12/2009 | Einarsson et al. |
| 2010/0028376 | A1 | 2/2010 | Einarsson et al. |
| 2010/0158830 | A1 | 6/2010 | Wei et al. |
| 2010/0216707 | A1 | 8/2010 | Bernard et al. |
| 2010/0322878 | A1 | 12/2010 | Stella et al. |
| 2011/0038830 | A1 | 2/2011 | Bernard et al. |
| 2011/0091439 | A1 | 4/2011 | Bernard et al. |
| 2011/0257020 | A1 | 10/2011 | Stella et al. |
| 2011/0257030 | A1 | 10/2011 | Stella et al. |
| 2011/0280822 | A1 | 11/2011 | Griffin et al. |
| 2012/0009285 | A1 | 1/2012 | Wei et al. |
| 2012/0184448 | A1 | 7/2012 | Stella et al. |
| 2012/0316095 | A1 | 12/2012 | Wei et al. |
| 2013/0149273 | A1 | 6/2013 | Wei et al. |
| 2017/0333315 | A1 | 11/2017 | Wei et al. |

FOREIGN PATENT DOCUMENTS

| | | |
|---|---|---|
| FR | 2 924 947 B1 | 3/2010 |
| FR | 2 925 314 B1 | 11/2012 |
| FR | 2 908 784 B1 | 12/2012 |
| FR | 2 924 613 B1 | 12/2012 |
| FR | 2 924 614 B1 | 12/2012 |
| GB | 2245585 A | 8/1992 |
| JP | 03095110 A2 | 4/1991 |
| JP | 04149112 A | 5/1992 |
| WO | WO 95/34280 A1 | 12/1995 |
| WO | WO 2009/081368 A2 | 7/2009 |
| WO | WO 2010/014614 A2 | 2/2010 |

* cited by examiner

COMPOSITIONS FOR TREATING SKIN

This application is a continuation of Ser. No. 15/669,001, filed Aug. 4, 2017, now abandoned, which is a continuation of Ser. No. 13/157,665, filed on Jun. 10, 2011, now U.S. Pat. No. 9,750,674, which claims benefit to Provisional Ser. No. 61/354,118, filed Jun. 11, 2010.

BACKGROUND OF THE INVENTION

Cleansing the skin is an activity that has been done for millennia. Over time, skin cleansing and related methods for cleansing skin have involved the utilization of soap, surfactants, and the like. Today, one prevalent form of skin cleansing compositions is the liquid form, often known as body wash. Users of body washed enjoy the conveniences that these compositions offer; however, the experience is not ideal. As the compositions for cleaning skin have evolved, the problems associated with these compositions have not. Many of the issues associated with current compositions and methods for skin cleansing, particularly body wash compositions, have not been addressed, and remain issues for users of these products today.

Structured surfactant compositions are useful commercially in order to suspend or stabilize dispersions, particularly dispersions of benefit agents which can be particles, domains, phases, emulsions, and the like. Structured compositions can be manufactured, packaged, delivered to the user while maintaining their physical integrity and aesthetics.

There are many means to provide structure, including surfactant phases, gel networks, crystalline domains, physical gels, polymeric structurants and polymer gels of various kinds, particle networks, and the like. Structured surfactants are a useful way to provide structure because the surfactant serves the dual functions of providing stability to the composition, and providing the lathering, cleansing, mildness and other functions typically associated with surfactant. This is efficient, cost effective, simple.

An important function of the surfactant is the ability of the surfactant to provide structure at full strength within a personal cleansing composition. However, a second function of the surfactant requires that upon dilution the personal care composition transition rapidly to free surfactant micelles that lather and clean. The necessity of providing both proper structure when at full strength, becoming micellar upon dilution has not been recognized in the art.

Modern personal care compositions, including body wash, utilize surfactants, such as sodium trideceth-3 sulfate (ST3S). While these surfactants demonstrate effective cleaning efficacy and enjoy commercial success, they have intrinsic problems associated with their use, specifically related to their ability to provide structuring, that are often cascading in nature. Typically, high amounts of ST3S must be present in order to properly stabilize any personal cleansing composition of which they are a part, as lower concentrations result in unstable products, which are not consumer acceptable. Moreover, the high surfactant levels make it difficult to form mild compositions. In order to boost structure, alkyl sulfates or coco monoethanolamide is often required to boost structure; however these compositions reduce mildness. Consequently, personal care compositions having higher concentrations for stability tend to be harsh on the skin. Efforts are made to add benefit agents to these compositions, with varied success, as large relative amounts of the benefit agents are required, often creating instability. Moreover, because of the large amount of surfactant, many benefit agents are not readily compatible within the tolerances allowed by the need for surfactants for stability. Finally, the attempts made to compensate for the above conditions often result in unacceptable lather properties. These problems have been systemic in both single phase as well as multi-phase compositions, as the surfactant concentrations within surfactant containing domains has resulted in compositions that fail to deliver a superior consumer experience. Additionally, compositions can also be overly structured, resulting in poor performance and lather formation.

Protection of the environment is also a growing concern. As such, there is a further desire to reduce the amount of surfactants within products. The reduction of surfactants within personal care compositions is made difficult by the need to maintain the efficacy of the benefit agents contained within.

There is, therefore, a need for a personal care composition that provides superior cleaning without the negative elements associated with body washes in the past, including high surfactant concentrations, harshness, stability issues and compatibility issues.

SUMMARY OF THE INVENTION

One aspect of this invention relates to a personal care composition comprising: at least a first phase and a second phase wherein: said first phase comprises: a) an aqueous structured surfactant phase comprising from about 5% to about 20%, by weight of said personal care composition, of STnS where n is between about 0.5 and about 2.7; b) at least one of the following: an amphoteric surfactant and a zwitterionic surfactant; c) a structuring system comprising: i. optionally, a non-ionic emulsifier; ii. optionally, from about 0.05% to about 5%, by weight of said personal care composition, of an associative polymer; iii. an electrolyte; and said second phase comprises: a) a benefit phase comprising from 0.1% to about 50%, by weight of said personal care composition, of a hydrophobic benefit agent; wherein said personal care composition is optionally substantially free of SLS; wherein said personal care composition comprises at least a 70% lamellar structure.

DETAILED DESCRIPTION OF THE INVENTION

Figure 1:
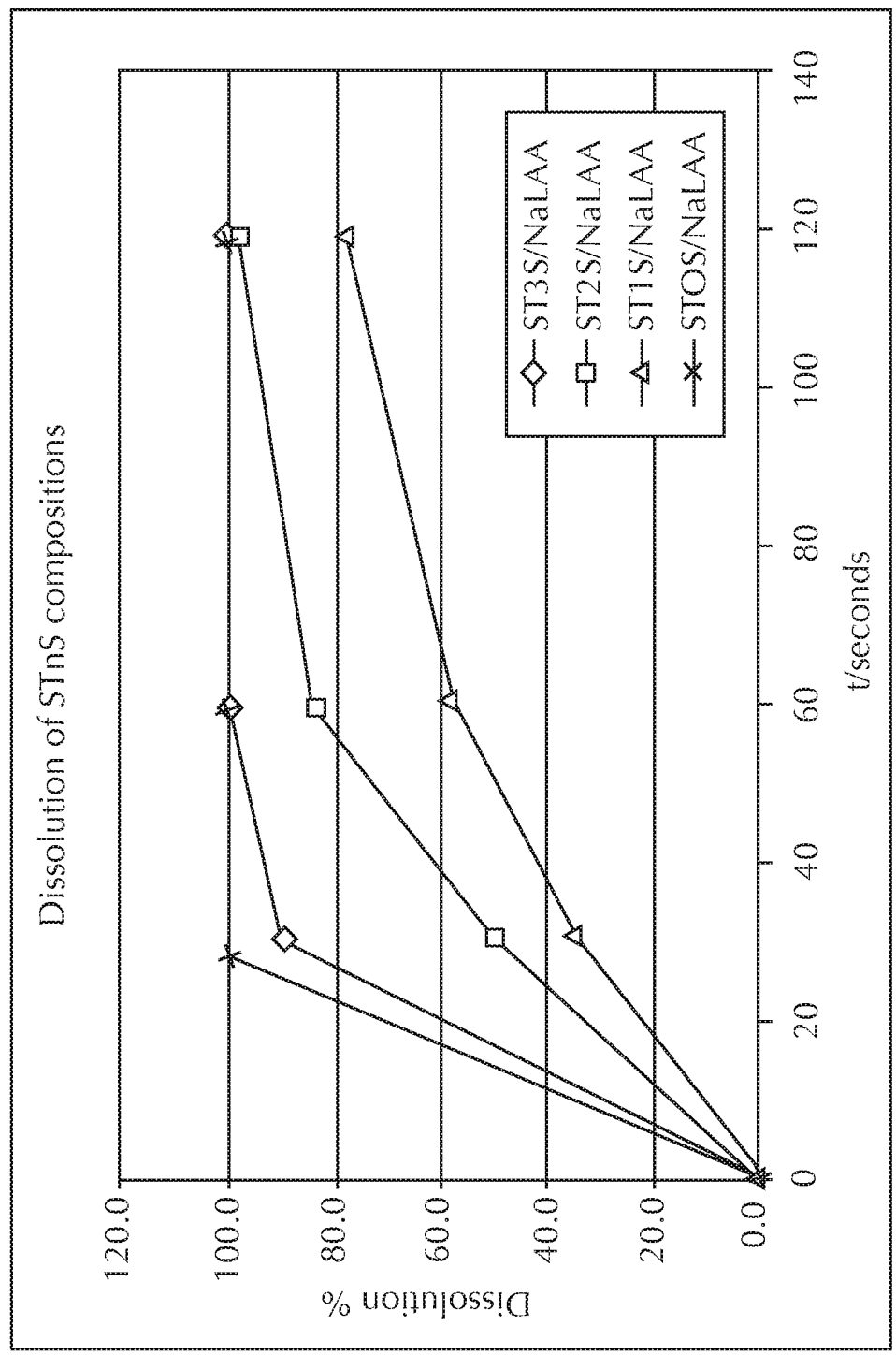
FIG. 1 is a graph of the dissolution of STnS series compositions.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

The term "anhydrous" as used herein, unless otherwise specified, refers to those compositions or materials containing less than about 10%, more preferably less than about 5%, even more preferably less than about 3%, even more preferably zero percent, by weight of water.

The term "multiphase" as used herein means that compositions comprise at least two phases which are chemically distinct (e.g. a surfactant phase and a benefit phase). Such phases are in direct physical contact with one another and are not separated by a barrier. In one aspect of the invention, the personal care composition can be a multiphase personal care composition where the phases of the personal care composition are blended or mixed to a significant degree. In another aspect of the invention, the personal care composition can be a multiphase personal care composition where the phases of the personal care composition are made to occupy separate but distinct physical spaces inside the package in which they are stored, but are in direct contact with one another (i.e., they are not separated by a barrier and they are not emulsified or mixed to any significant degree).

The term "package" includes any suitable container for a personal care compositions exhibiting a viscosity from about 1,500 centipoise (cP) to about 1,000,000 cP, including but not limited to bottle, tottle, tube, jar, non-aerosol pump and mixtures thereof.

The term "personal care composition" as used herein, refers to compositions intended for topical application to the skin or hair. The compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids. The personal care composition of the present invention is typically extrudable or dispensible from a package. The multiphase personal care compositions typically exhibit a viscosity of from about 1,500 centipoise (cP) to about 1,000,000 cP, as measured by as measured by the Viscosity Method as described in the commonly owned, patent application published on Nov. 11, 2004 under U.S. Publication No. 2004/0223991A1 entitled "Multi-phase Personal Care Compositions" filed on May 7, 2004 by Wei, et al. The multiphase personal care compositions of the present invention can be in the form of liquid, semi-liquid, cream, lotion or gel compositions intended for topical application to skin. Examples of personal care compositions of the present invention can include but are not limited to shampoo, conditioning shampoo, body wash, moisturizing body wash, shower gels, skin cleansers, cleansing milks, hair and body wash, in shower body moisturizer, pet shampoo, shaving preparations and cleansing compositions used in conjunction with a disposable cleansing cloth.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

The term "stable," as used herein, means that the multiphase personal care composition comprises less than 10% "third-phase" volume, more preferably less than 5% "third-phase" volume, most preferably less than 1% "third-phase" volume after undergoing the rapid protocol aging and third phase measurement as described below in the "Third-Phase" Method.

The term "structured," as used herein means having a rheology that confers stability on the multiphase composition. The degree of structure is determined by characteristics determined by one or more of the following methods: the Young's Modulus Method, Yield Stress Method, or the Zero Shear Viscosity Method or by the Ultracentrifugation Method, all in the Test Methods below. Accordingly, a surfactant phase of the multiphase composition of the present invention is considered "structured," if the surfactant phase has one or more of the following properties described below according to the Young's Modulus Method, Yield Stress Method, or the Zero Shear Viscosity Method or by the Ultracentrifugation Method. A surfactant phase is considered to be structured, if the phase has one or more of the following characteristics:

A. a Zero Shear Viscosity of at least about 100 Pascal-seconds (Pa-s), alternatively at least about 200 Pa-s, alternatively at least about 500 Pa-s, alternatively at least about 1,000 Pa-s, alternatively at least about 1,500 Pa-s, alternatively at least about 2,000 Pa-s; or B. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%; or most preferably at least about 90%.

C. A Young's Modulus of greater than about 2 Pascal (Pa), more preferably greater than about 10 Pa, even more preferably greater than about 20 Pa, still more preferably greater than about 30 Pa, 40 Pa, 50 Pa, 75 Pa, most preferably greater than 100 Pa.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized.

The term "STnS" as used herein, means sodium trideceth sulfate, where n is defined as the average number of moles of ethoxylate per molecule. Trideceth is a 13 carbon branched ethoxylated hydrocarbon comprising, in one embodiment, an average of at least 1 methyl branch per molecule.

The term "SLS" as used herein, means sodium lauryl sulfate.

The term "lather" as used herein, means the aerated foam which results from providing energy to aqueous surfactant mixtures, especially dilute mixtures. Lather is increased in micellar compositions compared to structured, e.g., lamellar compositions, so that a phase change during dilution to micelles typically increases lather.

As used herein "tottle" refers to a bottle which rests on neck or mouth which its contents are filled in and dispensed from, but it is also the end upon which the bottle is intended to rest or sit upon (e.g., the bottle's base) for storage by the consumer and/or for display on the store shelf (this bottle is referred to herein as a "tottle"). Typically, the closure on a tottle is flat or concave, such that the tottle, when stored, rests on the closure. Suitable tottles are described in the co-pending U.S. patent application Ser. No. 11/067,443 filed on Feb. 25, 2005 to McCall, et al, entitled "Multi-phase Personal Care Compositions, Process for Making and Providing, and Article of Commerce."

The term "visually distinct" as used herein, refers to a region of the multiphase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

One embodiment of the present invention relates to a personal care composition comprising: at least a first phase and a second phase wherein said first phase comprises an aqueous structured surfactant phase comprising a) from about 5% to about 20%, by weight of said personal care composition, of STnS where n is between about 1.2 and about 2.7; b) an amphoteric surfactant; c) a structuring system comprising i. optionally, a non-ionic emulsifier; ii. optionally, from about 0.05% to about 5%, by weight of said personal care composition, of an associative polymer; iii. an electrolyte; and said second phase comprises a) a benefit phase comprising from 1% to about 50%, by weight of said personal care composition, of a hydrophobic benefit agent; wherein said personal care composition is optionally substantially free of SLS; wherein said aqueous surfactant phase comprises at least a 70% of a structured phase, preferably a lamellar phase.

Without wishing to be bound by theory, it is believed that the surprising and unexpected results produced by the personal compositions of the present invention eliminate the problems associated with personal care compositions. Specifically, it has been found that the use of STnS, where n is less than 3, enables increased structure at low concentrations. This structure allows for improved stability at lower surfactant levels. The reduction in surfactant improves compatibility of benefit agents within personal care compositions. The improved capability allows for additional benefit agents to be utilized in increased amounts. The reduction in surfactant, along with the increased capability of benefit agents, provides for increased mildness of personal care compositions. Finally, the improved structure allows for improved lather at higher levels of dilution, as the micellar phase (where lather is capable of being formed) occurs at a higher level of dilution.

Cleansing Phase

One of the phases of the personal care composition of the present invention is a cleansing phase, which is a surfactant phase. The cleansing phase is comprised of a structured domain that comprises a surfactant and optionally a cosurfactant. The structured domain is preferably an opaque structured domain, which is preferably a lamellar phase. The lamellar phase can provide resistance to shear, adequate yield to suspend particles and droplets and at the same time provides long term stability, since it is thermodynamically stable. The lamellar phase tends to have a viscosity that minimizes the need for viscosity modifiers.

The surfactant of the present invention is sodium trideceth (n) sulfate, hereinafter STnS, wherein n defines the average moles of ethoxylation. In one embodiment, n ranges from greater than 0 to 3, alternatively from 0.5 to 2.7, alternatively from 1.1 to 2.5, alternatively from greater than 0 to 2.5, alternatively from 1.8 to 2.2, alternatively about 2. It is understood that a material such as ST2S, for example, may comprise a significant amount of molecules which have no ethoxylate, 1 mole ethoxylate, 3 mole ethoxylate, and so on in a distribution which can be broad, narrow or truncated, still comprising ST2S wherein the average of the distribution is about 2.

In one embodiment, the personal care compositions of the present invention comprise from about 3% to about 20% STnS, alternatively from about 5% to about 15% STnS, alternatively from about 7% to about 13% STnS, alternatively from about 5% to about 13% STnS, alternatively from about 1% to about 13% STnS.

Figure 5:
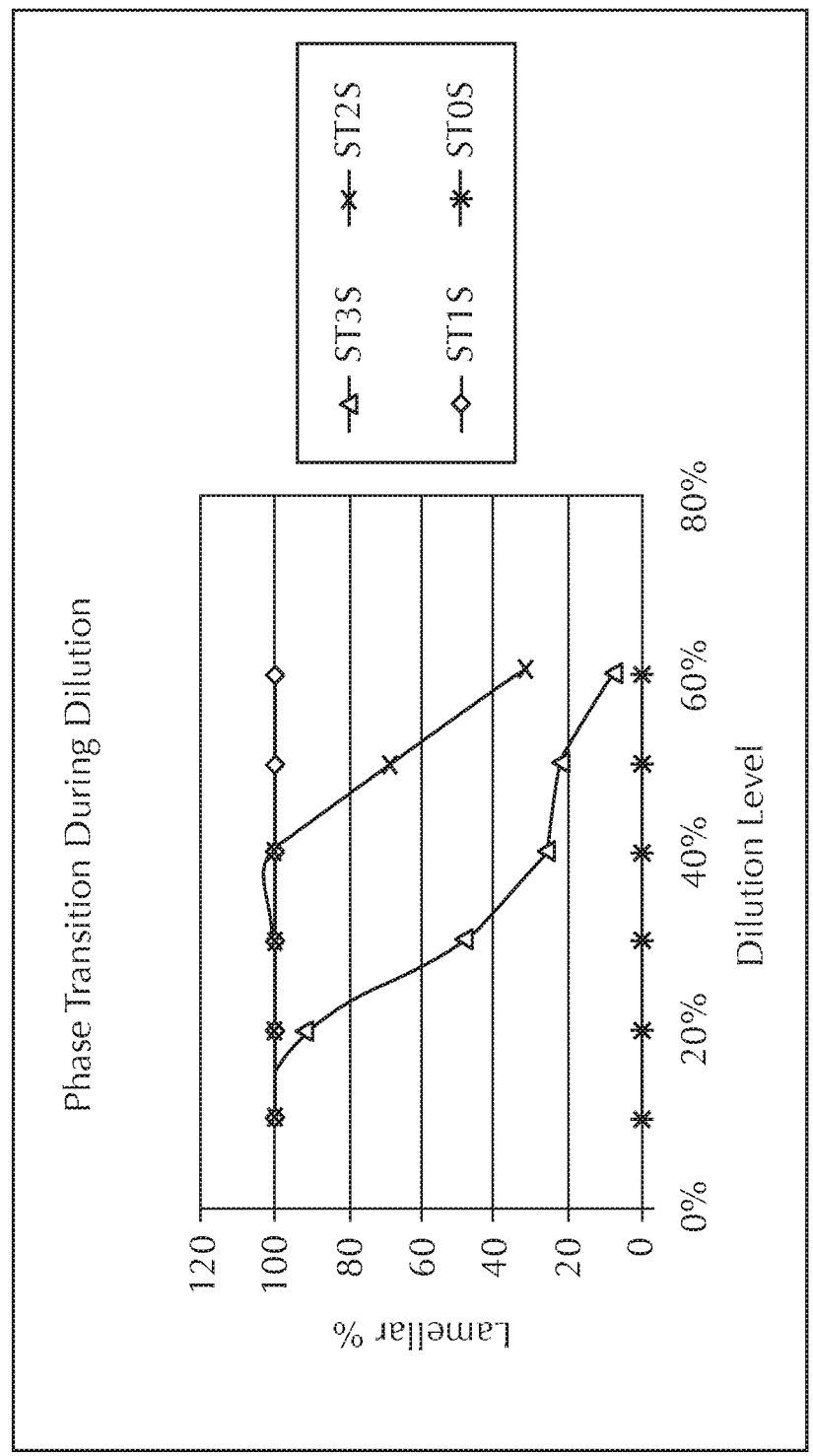
FIG. 5 is a graph of the phase transition during dilution of the STnS series compositions.

It has been discovered that STnS having fewer than 3 moles of ethoxylation provides surprising structural improvements. FIG. 5 illustrates these improvements by comparing a composition comprising, ST1S, ST2S, and ST3S. At increasing levels of dilution, ST3S begins to transition from a lamellar structure to a micellar structure beginning at about the 19% surfactant level. As such, dilution beyond this level results in a loss of structure. This loss of structure has, until now, necessitated higher concentrations of surfactant to be present within a package. ST2S compositions can remain well structured until a dilution point of 13% surfactant within this example, allowing for the transition to a more micellar structure at much higher dilution levels. ST1S compositions can remain lamellar at even lower surfactant concentrations.

While sodium trideceth sulfate has been disclosed and commercialized, the utilization and benefits of sodium trideceth sulfate having lower ethoxylation values have been unknown, a rationale further supported by the general popularity of ST3S within commercially available products, and the lack of commercial availability of lower ethoxylation products. It is this unknown and surprising result that enables various benefits of the personal care compositions of the present invention, including improved stability, mildness, compatibility, and lather creation.

Without intending to be limited by theory, the rationale for improved function of STnS, where n is below 3, can be illustrated utilizing dissipative particle dynamics (DPD) simulations. As related to STnS, surfactant aggregates form curved surfaces based on the surfactant shape and interactions between molecules, leading to surfactant architectures which are phases; and to degree of structure of a phase as measured by rheology parameters such as zero shear viscosity. To measure the amount of surfactant curvature, molecular simulations were carried out using DPD by breaking surfactant atoms into beads, where a bead represents typically 3-4 heavy atoms. Simulations were performed in a cube cell with an edge length of approximately 25 nm. The compositions of the simulation boxes varied in average amount of ethoxylation (n=0 to 3) of STnS. Assembly of surfactants into aggregates starting from random positions was observed during the course of the simulations. DPD Curvature was computed as an average curvature over multiple independent simulations for the surfactant head group-water surface of all resulting objects in a simulation frame, including all bilayers and micelles, and is a relative measure of the average deviation of the colligative surfactant head group surface from flat. DPD Curvature of zero are flat layers with edge defects, which do not form multilamellar vesicles and hence are not expected to exhibit structured rheology, e.g., high zero shear viscosity. At DPD Curvature of about 0.07 and higher, elongated micelle structures are observed to form. At intermediate DPD curvature, curved bilayers can form multilamellar vesicles, leading to high zero shear viscosity and stable compositions.

Figure 9:
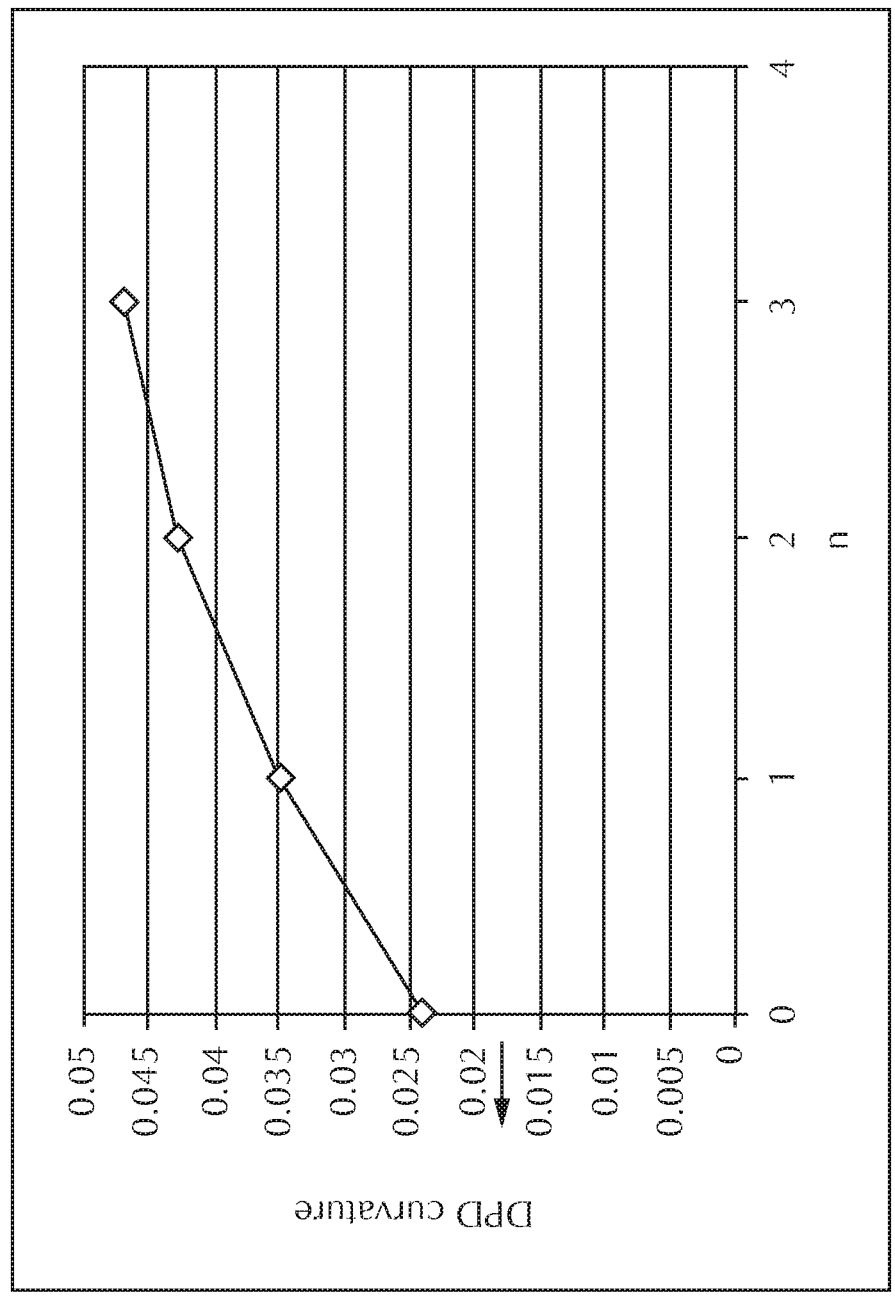
FIG. 9 is a graph of the DPD Curvature of the STnS series compositions.

As illustrated in FIG. 9, the simulation results demonstrate bilayers formed from the STnS compositions have lower DPD Curvature of surfactant aggregates with decreasing n. DPD Curvature of ST0S compositions is too low to form compact vesicle structures, whereas the DPD curvature of ST3S compositions is too high so zero shear viscosity is not as high as compared to ST2S compositions of the present invention. Preferred structure is observed for compositions of the present invention having DPD Curvature between about 0.03 and 0.045.

Often, STnS is combined with SLS in order to form a surfactant system. In one embodiment, the personal care compositions of the present invention comprise less than about 5% SLS, alternatively less than about 4% SLS, alternatively less than about 3% SLS, alternatively less than about 2% SLS, alternatively less than about 1% SLS, alternatively between about 0.1% SLS and about 2% SLS, alternatively about 0% SLS. Without wishing to be bound by theory, it is believed that the presence of SLS increases the harshness of the personal care composition, negating at least in part the mildness benefits and/or the efficacy of the benefit agents within the personal care composition.

Cosurfactant

The personal care compositions of the present invention further comprises a cosurfactant. Cosurfactants in the present invention comprise from about 0.1% to 20%, alternatively from about 2% to about 10% of the personal care composition. Cosurfactants of the present invention comprise amphoteric surfactants, zwitterionic surfactants, and mixtures thereof. In one embodiment, the personal care composition comprises at least one amphoteric surfactant and/or at least one zwitterionic surfactant. Amphoteric surfactant suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. In one aspect, the multiphase personal care composition can comprise an amphoteric surfactant that is selected from the group consisting of sodium lauroamphoacetate, sodium cocoamphoactetate, disodium lauroamphoacetate disodium cocodiamphoacetate, and mixtures thereof. Moreover, amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

Associative Polymer

In one embodiment, the associative polymer is a crosslinked, alkali swellable, associative polymer comprising acidic monomers and associative monomers with hydrophobic end groups, whereby the polymer comprises a percentage hydrophobic modification and a hydrophobic side chain comprising alkyl functional groups having a length. Without intending to be limited by theory, it is believed that the acidic monomers contribute to the ability of the polymer to swell in water upon neutralization of the acidic groups; and associative monomers anchor the polymer into structured surfactant hydrophobic domains, e.g., lamellae, to confer structure to the surfactant compositions and keep the polymer from collapsing and losing effectiveness in the presence of electrolyte. The crosslinked, associative polymer comprises a percentage hydrophobic modification, which is the mole percentage of monomers expressed as a percentage of the total number of all monomers in the polymer backbone, including both acidic and other non-acidic monomers. The percentage hydrophobic modification of the polymer, hereafter % HM, can be determined by the ratio of monomers added during synthesis, or by analytical techniques such as proton nuclear magnetic resonance (NMR). The alkyl side chain length can be determined similarly. Monomers comprising only 2 or fewer alkyl hydrocarbons (e.g., ethyl, methyl) are not considered associative for the purposes of the present invention, all side chains having more than 2 carbons being associative. Associative alkyl side chains comprise for example butyl, propyl, stearyl, steareth, cetyl, lauryl, laureth, octyl, behenyl, beheneth, steareth, or other linear, branched, saturated or unsaturated alkyl or alketh hydrocarbon side chains.

It has been discovered that crosslinked, associative polymers having preferred % HM and preferred carbon numbers of the hydrophobic end groups of the alkyl side chains provide significant enhancement of structure to structured surfactant compositions of the present invention, especially to inventive compositions comprising reduced levels of surfactant; and provide said structure at surprisingly low levels of polymer structurant. Concentrations of associative polymer of up to 5% or even 10% are taught in the art to obtain a sufficient amount structure, for example the exemplary compositions of U.S. Pat. No. 7,119,059 (Librizzi, et al) and U.S. Pat. No. 6,897,253 (Schmucker-Castner, et al). Inventors have found when the associative polymer % HM and the alkyl side chain number of carbons is optimized, structure of the aqueous structured surfactant phase is increased using only less than 3 wt % associative polymer as a percentage of the aqueous structured surfactant phase, preferably less than 2%, more preferably less than 1%, and even only about 0.2% of the phase, as demonstrated by the inventive examples hereinbelow.

The acidic monomer can comprise any acid functional group, for example sulfate, sulfonate, carboxylate, phosphonate, or phosphate or mixtures of acid groups. In one embodiment, the acidic monomer comprises a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer comprises a hydrophobic end group and a polymerizable component, e.g., vinyl, which are attached. The hydrophobic end group can be attached to the polymerizable component, hence to the polymer chain, by different means but preferably is attached by an ether or ester or amide functionality, such as an alkyl acrylate or a vinyl alkanoate monomer. The hydrophobic end group can also be separated from the chain, for example by an alkoxy ligand such as an alkyl ether. In one embodiment, the associative monomer is an alkyl ester, alternatively an alkyl (meth) acrylate, where (meth)acrylate is understood to mean either methyl acrylate or acrylate or mixtures of the two.

In one embodiment, the hydrophobic end group of the associative polymer is incompatible with the aqueous phase of the composition and associates with the lathering surfactant hydrophobe components of the current invention. Without intending to be limited by theory, it is believed that the longer alkyl chains of the structuring polymer hydrophobe end groups increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) are also effective, so a range of preferred materials balancing these opposing requirements, limited by solubility of the total molecule itself, is ideal. Polymers having short alkyl side chains, e.g., less than 6 carbons, are ineffective for the present invention. Inventors have discovered an ideal range of hydrophobic end group carbon numbers combined with an optimal percentage of hydrophobic monomers expressed as a percentage of the polymer backbone provides increased structure to the lathering, structured surfactant composition at low levels of polymer structurant.

Preferred associative polymers comprise about C16 (cetyl) alkyl hydrophobic side chains with about 0.7% hydrophobic modification, but the percentage hydrophobic modification can be up to the aqueous solubility limit in surfactant compositions, e.g., up to 2% or 5% or 10%. An exemplary preferred associative polymer is Aqupec SER-300 made by Sumitomo Seika of Japan, which is Acrylates/C10-30 alkyl acrylate crosspolymer and comprises stearyl side chains with less than about 1% HM. Other preferred associative polymers comprise stearyl, octyl, decyl and lauryl side chains. Preferred associative polymers are Aqupec SER-150 (acrylates/C10-30 alkyl acrylates crosspolymer) comprising about C18 (stearyl) side chains and about 0.4% HM, and Aqupec HV-701EDR which comprises about C8 (octyl) side chains and about 3.5% HM. Another preferred polymer is Stabylen 30 manufactured by 3V Sigma S.p.A., which has branched isodecanoate hydrophobic associative side chains. Importantly, inventors have discovered not all crosslinked, associative polymers are effective, and many are deleterious to structure. Associative polymers having hydrophobe side chains with fewer than 7 carbons and having % HM greater than about 25% or about 50% are dispreferred. For example, Carbopol Aqua SF-1 (crosslinked acrylates copolymer) having average 4.5 carbon alkyl side chains and more than 50% HM is deleterious to structure as demonstrated by the examples hereinbelow.

Deposition Polymers

The personal care compositions of the present invention can additionally comprise an organic cationic deposition polymer in the one or more phases as a deposition aid for the benefit agents described herein. Suitable cationic deposition polymers for use in the compositions of the present invention contain cationic nitrogen-containing moieties such as quaternary ammonium moieties. Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

In one embodiment, the deposition polymers of the present invention have a cationic charge density from about 0.8 meq/g to about 2.0 meq/g, alternatively from about 1.0 meq/g to about 1.5 meq/g.

Water

The surfactant phase of the present invention also comprises water. In one embodiment, the surfactant phase of the personal care composition comprises from about 10% to about 90%, alternatively from about 40% to about 85%, alternatively from about 60% to about 80% by weight water.

Benefit Phase

The personal care compositions of the present invention comprise a benefit phase. The benefit phase in the present invention is preferably hydrophobic or essentially anhydrous and can be substantially free of water. The benefit phase can be substantially free or free of surfactant.

The benefit phase typically comprises benefit agents. Benefit agents include water insoluble or hydrophobic benefit agents. The benefit phase may comprise from about 0.1% to about 50%, preferably from about 1% to about 30%, more preferably from about 5% to about 30%, by weight of the personal care composition, of a benefit agent.

The hydrophobic skin benefit agent for use in the benefit phase of the composition has a Vaughan Solubility Parameter (VSP) of from about 5 to about 15, preferably from about 5 to less than 10. These solubility parameters are well known in the formulation arts, and are defined by Vaughan in Cosmetics and Toiletries, Vol. 103, p47-69, October 1988.

Non-limiting examples glycerides suitable for use as hydrophobic skin benefit agents herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as hydrophobic skin benefit agents herein include acetylated monoglycerides.

Non-limiting examples of alkyl esters suitable for use as hydrophobic skin benefit agents herein include isopropyl esters of fatty acids and long chain esters of long chain (i.e. C10-C24) fatty acids, e.g. cetyl ricinoleate, non-limiting examples of which incloude isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein include oleyl myristate, oleyl stearate, oleyl oleate, and combinations thereof.

Non-limiting examples of polyglycerin fatty acid esters suitable for use as hydrophobic skin benefit agents herein include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic skin benefit agents herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic skin benefit agents herein include dimethicone copolyol, dimethylpolysiloxane, diethylpolysiloxane, mixed C1-C30 alkyl polysiloxanes, phenyl dimethicone, dimethiconol, and combinations thereof. Preferred are non-volatile silicones selected from dimethicone, dimethiconol, mixed C1-C30 alkyl polysiloxane, and combinations thereof. Non-limiting examples of silicone oils useful herein are described in U.S. Pat. No. 5,011,681 (Ciotti et al.).

Still other suitable hydrophobic skin benefit agents include milk triglycerides (e.g., hydroxylated milk glyceride) and polyol fatty acid polyesters.

Still other suitable hydrophobic skin benefit agents include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof. Also suitable benefit agents include glycerol monooleate.

Skin Actives and Solid Particles

The compositions may optionally comprise the following skin benefit ingredients for enhanced delivery of these benefit materials on skin.

A) Desquamation Actives

Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett. Preferred concentrations of desquamation actives range from about 0.1% to about 10%, more preferably from about 0.2% to about 5%, even more preferably from about 0.5% to about 4%, by weight of the personal cleansing composition.

Another desquamation system that is suitable for use herein contains salicylic acid and zwitterionic surfactants and is described in U.S. Pat. No. 5,652,228 to Bissett. Zwitterionic surfactants such as described in these applications are also useful as desquamatory agents herein, with cetyl betaine being particularly preferred.

B) Anti-Wrinkle Actives/Anti-Atrophy Actives

Anti-wrinkle actives or anti-atrophy actives include sulfur-containing D and L amino acids and their derivatives and salts, particularly the N-acetyl derivatives. A preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like).

Hydroxy acids as skin active agents herein include salicylic acid and salicylic acid derivatives, preferred concentrations of anti-wrinkle/anti-atrophy actives range from about 0.01% to about 50%, more preferably from about 0.1% to about 10%, even more preferably from about 0.5% to about 2%, by weight of the personal cleansing composition.

Other non-limiting examples of suitable anti-wrinkle actives for use herein are described in U.S. Pat. No. 6,217,888, issued to Oblong et al.

C) Anti-Oxidants/Radical Scavengers

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. The preferred concentrations range from about 0.1% to about 10%, more preferably from about 1% to about 5%, by weight of the personal cleansing composition.

D) Chelators

The term "chelating agent" or "chelator" refers to those skin active agents capable of removing a metal ion from a system by forming a complex so that the metal ion cannot readily participate in or catalyze chemical reactions.

The chelating agents as skin active agents for use herein are preferably included at concentrations ranging from about 0.1% to about 10%, more preferably from about 1% to about 5%, by weight of the personal cleansing composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. A preferred chelating agent for use in the compositions of the present invention includes disodium EDTA, and derivatives thereof.

E) Anti-Cellulite Agents

Non-limiting examples of anti-cellulite agents include xanthine compounds such as caffeine, theophylline, theobromine, aminophylline, and combinations thereof. Anti-cellulite agents are preferably included at concentrations ranging from about 0.1% to about 10%, more preferably from about 1% to about 5%, by weight of the personal cleansing composition.

F) Tanning Actives

Non-limiting examples of such tanning agents include dihydroxyacetone, which is also known as DHA or 1,3-dihydroxy-2-propanone. Tanning actives are preferably included at concentrations ranging from about 0.1% to about 10%, more preferably from about 1% to about 5%, by weight of the personal cleansing composition.

G) Skin Lightening Agents

Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract). Non-limiting examples of skin lightening agents suitable for use herein also include those described in WO 95/34280, WO 95/07432, and WO 95/23780. Skin lightening agents are preferably included at concentrations ranging from about 0.1% to about 10%, more preferably from about 1% to about 5%, by weight of the personal cleansing composition.

H) Skin Soothing and Skin Healing Actives

Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate. Skin soothing and skin healing actives are preferably included at concentrations ranging from about 0.1% to about 10%, more preferably from about 1% to about 5%, by weight of the personal cleansing composition.

I) Antimicrobial Actives

Non-limiting examples of antimicrobial actives for use herein includes β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetra¬cycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sul¬fate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione (which can also be combined a zinc salt such as zinc carbonate), clotrimazole, and combinations thereof.

Antimicrobials are preferably included at concentrations ranging from about 0.1% to about 10%, more preferably from about 1% to about 5%, by weight of the personal cleansing composition.

J) Sunscreen Actives

Non-limiting examples of sunscreen actives, either organic or inorganic for use herein are described below.

Among the inorganic sunscreens useful hererin are metallic oxides such as titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500nm, and mixtures thereof.

The concentration of the sunscreen active for use in the composition preferably ranges from about 0.1% to about 20%, more typically from about 0.5% to about 10%, by weight of the composition. Exact amounts of such sunscreen actives will vary depending upon the sunscreen or sunscreens chosen and the desired Sun Protection Factor (SPF).

A wide variety of conventional organic sunscreen actives are also suitable for use herein, non-limiting examples of which include p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pylenglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane. Among these sunscreens, preferred are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and combinations thereof.

K) Solid Particulates

The compositions of the present invention may comprise a solid particle. Nonlimiting examples of the solid particles include: interference pigment, multi-layered pigment, metallic particle, solid and liquid crystals, or combinations thereof.

An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. The interference pigments of the multi-phased personal care compositions preferably comprises no more than about 20 weight percent of the composition, more preferably no more than about 10 weight percent, even more preferably no more than about 7 weight percent, and still more preferably no more than about 5 weight percent of the multi-phased personal care composition. The interference pigment of the multi-phased personal care composition preferably comprises at least about 0.1 weight percent of the multi-phased personal care composition, more preferably at least about 0.2 weight percent, even more preferably at least about 0.5 weight percent, and still more preferably at least about 1 weight percent by weight of the composition. When pigment is applied and rinsed as described in the Pigment Deposition Tape Strip Method as described in copending application Ser. No. 60/469,075 filed on May 8, 2003, the deposited pigment on the skin is preferably at least 0.5 µg/cm2, more preferably at least 1 µg/cm2, and even more preferably at least 5 µg/cm2.

In an embodiment of the present invention the interference pigment surface is either hydrophobic or has been hydrophobically modified. The Particle Contact Angle Test as described in application Ser. No. 60/469,075 filed on May 8, 2003 is used to determine contact angle of interference pigments. The greater the contact angle, the greater the hydrophobicity of the interference pigment. The interference pigment of the present invention possess a contact angle of at least 60 degrees, more preferably greater than 80 degrees, even more preferably greater than 100 degrees, still more preferably greater than 100 degrees. The hydrophobically modified interference pigment or HMIP allows for the entrapment of the HMIP within the phases and greater deposition of the HMIP. Preferably the ratio of HMIP to a phase is 1:1 to about 1:70, more preferably 1:2 to about 1:50, still more preferably 1:3 to about 1:40 and most preferably 1:7 to about 1:35.

In an embodiment of the present invention the HMIP's are preferably entrapped within the benefit phase. This necessitates that the benefit phase particle size is generally larger than the HMIP. In a preferred embodiment of the invention, the benefit phase particles contain only a small number of HMIPs per benefit particles. Preferably this is less than 20, more preferably less than 10, most preferably less than 5. These parameters, the relative size of the benefit droplets to the HMIP and the approximate number of HMIP particles per benefit particles, can be determined by using visual inspection with light microscopy.

The HMIP and the benefit phase can be mixed into the composition via a premix or separately. For the case of separate addition, the hydrophobic pigments partition into the benefit phase during the processing of the formulation. The HMIP of the present invention preferably has a hydrophobic coating comprising no more than about 20 weight percent of the total particle weight, more preferably no more than about 15 weight percent, even more preferably no more than about 10 weight percent. The HMIP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

Optional Ingredients

While not essential for the purposes of the present invention, the non-limiting list of materials, in addition to the previously disclosed, optional materials, illustrated hereinafter are suitable for use in the personal care composition, and may be desirably incorporated in certain embodiments, for example to assist or enhance cleansing performance, for treatment of the skin, or to modify the aesthetics of the personal care composition as is the case with perfumes, colorants, dyes or the like. Optional materials useful in the products herein are categorized or described by their cosmetic and/or therapeutic benefit or their postulated mode of action or function. However, it is to be understood that the active and other materials useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed. The precise nature of these optional materials, and levels of incorporation thereof, will depend on the physical form of the composition and the nature of the cleansing operation for which it is to be used. The optional materials are usually formulated at less than about less than about 6%, less than about 5%, less than about 4%, less than about 3%, less than about 2%, less than about 1%, less than about 0.5%, less than about 0.25%, less than about 0.1%, less than about 0.01%, less than about 0.005% of the personal care composition.

To further improve stability under stressful conditions such as high temperature and vibration, it is preferable to adjust the densities of the separate phases such that they are substantially equal. To achieve this, low density microspheres can be added to one or more phases of the personal care composition, preferably the structured surfactant phase. Personal care composition that comprises low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

Other non limiting optional ingredients that can be used in the personal care composition of the present invention can comprise an optional benefit component that is selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl acetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. In one aspect, the multiphase personal care composition may comprise from about 0.1% to about 4%, by weight of the multiphase personal care composition, of hydrophobically modified titanium dioxide.Other optional ingredients are most typically those materials approved for use in cosmetics and that are described in the CTFA Cosmetic Ingredient Handbook, Second Edition, The Cosmetic, Toiletries, and Fragrance Association, Inc. 1988, 1992.

Test Methods

The current invention utilizes a number of test methods to determine various metrics of structure. The methodology for these tests and associated examples are illustrated below.

Zero Shear Viscosity and Young's Modulus Methods

The Zero Shear Viscosity of a material which is a phase or a composition of the present composition, can be measured either prior to combining in the composition, after preparing a composition, or first separating a phase or component from a composition by suitable physical separation means, such as centrifugation, pipetting, cutting away mechanically, rinsing, filtering, or other separation means.

A controlled stress rheometer such as a TA Instruments AR2000 Rheometer is used to determine the Zero Shear Viscosity. The determination is performed at 25° C. with the 4 cm diameter parallel plate measuring system and a 1 mm gap. The geometry has a shear stress factor of 79580 m−3 to convert torque obtained to stress. Serrated plates can be used to obtain consistent results when slip occurs.

First the material is positioned on the rheometer base plate, the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset, which can influence results obtained. If the material comprises particles discernible to the eye or by feel (beads, e.g.) which are larger than about 150 microns in number average diameter, the gap setting between the base plate and upper plate is increased to the smaller of 4 mm or 8-fold the diameter of the 95th volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. If the measurement result is incomplete, for example if material is observed to flow from the gap, results obtained are evaluated with incomplete data points excluded. If there are insufficient points to obtain an accurate measurement, the measurement is repeated with increased number of sample points.

The Young's Modulus (Pa) is obtained by graphing the Stress (Pa) vs. Strain (unitless) and obtaining the slope of the regression line of the initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-sec) for viscosity data obtained between and including 0.1 Pa and the point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Compositions of the present invention have a Zero Shear Viscosity of at least about 100 Pa-s, alternatively at least about 300 Pa-s, alternatively at least about 500 Pa-s, alternatively at least about 1000 Pa-s, alternatively at least about 1500 Pa-s, alternatively at least about 2000 Pa-s.

Compositions of the present invention have a Young's Modulus of at least about 2 Pa, alternatively at least about 5 Pa, alternatively at least about 10 Pa, alternatively at least about 20 Pa, alternatively at least about 30 Pa, alternatively at least about 40 Pa, alternatively at least about 50 Pa, alternatively at least about 75 Pa.

Ultracentrifugation Method

The Ultracentrifugation Method is a physical method used to determine amount of structure in a composition or a subset of a composition. The method is also used to determine the rate at which a structured surfactant composition dissolves upon dilution to present effective amounts of surfactant to the cleaning environment proximal to surfaces.

A composition is separated by ultracentrifuge into separate but distinguishable layers. The multiphase personal care composition of the present invention can have multiple distinguishable layers (e.g., a structured surfactant layer, and a benefit layer).

First, dispense about 4 grams of composition into a Beckman Centrifuge Tube (11×60 mm) to fill the tube. Next, dilute the composition to a 10% Dilution Level using 90% of the composition and 10% DI water using an appropriate mixer and dispense the same amount of composition into a companion centrifuge tube. Continue to dilute the composition and fill tubes in the same manner until a 60% Dilution Level is obtained for the composition using 40% of the composition with 60% DI water. Place the centrifuge tubes in an ultracentrifuge (Beckman Model L8-M or equivalent) using a sling rotor and ultracentrifuge using the following conditions: 50,000 rpm, 2 hours, and 40° C.

Measure the relative phase volumes of the phases the composition by measuring the height of each layer using an Electronic Digital Caliper (within 0.01 mm). Layers are identified by those skilled in the art by physical observation techniques paired with chemical identification if needed. For example, the structured surfactant layer is identified by transmission electron microscopically (TEM), polarized light microscopy, and/or X-ray diffraction for the present invention as a structured lamellar phase comprising multi-lamellar vesicles, and the hydrophobic benefit layer is identified by its low moisture content (less than 10% water as measured by Karl Fischer Titration). The total height $H_a$ is measured which includes all materials in the ultracentrifuge tube. Next, the height of each layer is measured from the bottom of the centrifuge tube to the top of the layer, and the span of each layer algebraically determined by subtraction. The benefit layer may comprise several layers if the benefit phase has more than one component which may phase splits into liquid and waxy layers, or if there is more than one benefit component. If the benefit phase splits, the sum of the benefit layers measured is the benefit layer height, $H_b$. Generally, a hydrophobic benefit layer when present, is at the top of the centrifuge tube. The surfactant phase may comprise several layers or a single layer, $H_c$. There may also be a micellar, unstructured, clear isotropic layer at the bottom or next to the bottom of the ultracentrifuge tube. The layers immediately above the isotropic phase generally comprise higher surfactant concentration with higher ordered structures (such as liquid crystals). These structured layers are sometimes opaque to naked eyes, or translucent, or clear. There may be several structured layers present, in which case $H_c$ is the sum of the individual structured layers. If any type of polymer-surfactant phase is present, it is considered a structured phase and included in the measurement of $H_c$. The sum of the aqueous phases is $H_s$.

Finally, the structured domain volume ratio is calculated as follows:

Structured Domain Volume Ratio=$H_c/H_s*100\%$

If there is no benefit phase present, use the total height as the surfactant layer height, $H_s=H_a$. For the present invention, the Structured Domain Volume Ratio is the Lamellar Phase %. The measurement is made for each dilution prepared and centrifuged, i.e., the Structured Domain Volume Ratio is determined for the composition, and for 90%, 80%, 70% and 60% dilutions prepared as indicated above.

The highest amount of dilution (i.e., the lowest Dilution Level) wherein the composition maintains at least 95% Lamellar Phase % is an indicator of amount of structure for compositions having varying n values for STnS.

In one embodiment, the highest dilution wherein the composition has at least 95% lamellar phase is greater than about 15%, alternatively greater than about 25%, alternatively greater than about 35%.

In one embodiment, the composition has a Structured Domain Volume Ratio of at least about 40%, alternatively at least about 45%, alternatively at least about 50%, alternatively at least about 55%, alternatively at least about 60%, alternatively at least about 65%, alternatively at least about 70%, alternatively at least about 75%, alternatively at least about 80%, alternatively at least about 85%, and alternatively greater than about 90% by volume of the aqueous surfactant composition.

Ultracentrifugation Dilution Method

The Ultracentrifugation Dilution Method is a physical method used to determine amount of structure in a composition at a certain point in its dilution profile, which relates to the ability of the composition to lather. The Ultracentrifugation Dilution Method utilizes the results from the Ultracentrifugation Method at the 50% dilution point. When consumers use surfactant compositions with an implement such as a washcloth or a Puff, about 10 ml of composition is typically dosed onto the implement which can contain about 10 ml of water therein. Consumers agitate to generate lather, requiring the composition to rapidly dissolve at this dilution strength. The ability of structured surfactant compositions to dissolve at 50% Dilution % is measured by the method.

The method is identical in all its details to the Ultracentrifugation Method. The result at 50% Dilution % is obtained for a composition and is expressed as the Diluted 50% Lamellar Phase Volume.

Results from the Ultracentrifugation Dilution Method parallel results obtained for the Dissolution Rate Test for the compositions of the current invention comprising STnS, affirming the relationship between high structure and reduced lather, and vice versa, leading to improved stability and use aesthetics within a narrower range of n values for STnS. The ST0S composition of Example 4 being relatively unstructured, has low structure upon dilution, but is unsuitable for the purposes of a structured surfactant composition due to its inability to provide requisite stabilization to a composition based on its rheology. The ST3S composition of Example 1 has sufficient structure and dilutes rapidly to micellar surfactants useful for lather and cleaning, but disadvantageously these ST3S compositions cannot readily be formulated into compositions comprising reduced surfactant levels; they will always remain costly, inefficient, environmentally less preferred, and less mild. The ST1S composition of Example 3 has a Diluted 50% Lamellar Phase Volume of 100%, which will result in poor lather and cleaning characteristics in many use modes. The ST2S composition of Example 2 demonstrates versatility in that it has a high degree of structure yet dilutes sufficiently to provide a good lather result, the lather performance supported by its Diluted 50% Lamellar Phase Volume value of 70%. ST2S compositions can be prepared at reduced surfactant levels, for example at 15%, or 12%, or 10% or 8% or even 6% surfactant and retain many of the preferred features of the present invention.

In one embodiment of the present invention, the Diluted 50% Lamellar Phase Volume for a composition of the present invention is less than about 90%, alternatively less than about 80%, alternatively less than 75%.

Dissolution Rate Method

Structured compositions are prone to slow dissolution, hence poor lather characteristics and cleaning can result. Slowly dissolving structured surfactant phases are largely behind the development of the "Puff" implement many years ago, an agitating implement that encourages dissolution, lather and cleaning. Lather and cleaning result from the ability of aqueous surfactant molecules to diffuse to and stabilize air interfaces and soil surfaces. When surfactants remain locked into lamellar or other organized structures, they are unable to diffuse in the aqueous phase and so must first dissolve as individual surfactant monomers and micelles in order to be effective. Dilution and agitation encourage dissolution during use. The Dissolution Rate Method measures the extent of dissolution of a surfactant composition in water.

A straight walled glass beaker is obtained having an inside diameter (i.d.) of 63 mm and an inside height of 87 mm, e.g. Pyrex 250 ml (No. 1000) which are widely available. 150 grams of distilled water at ambient temperature (75° F.) is poured into the beaker. A Teflon ® coated magnetic stir bar is added to the beaker. The stir bar is nominally 1.5 inches long×5/16 inches diameter and octagonally shaped viewed from the end and has a 1/16 in. wide molded pivot ring around its center where the diameter is increased to about 0.35 in. Spinbar ® magnetic stir bars are available from Sigma Aldrich Corp. worldwide including Milwaukee, Wis., USA and at www.sigmaaldrich.com.

Measure and record the Initial Water Conductivity of the water using a conductivity meter, e.g., a Mettler-Toledo SevenMulti meter with InLab740 probe, and record the value. The conductivity of the water should be about 2 microSemens/cm (uS/cm) or less to indicate a low level of dissolved solids present. Remove the conductivity probe from the water and place the beaker onto a digitally controlled laboratory stirrer, for example Ika® Werke RET Control-visc available, e.g., from DivTech Equipment Co, Cincinnati, Ohio, USA. The beaker is centered on the stirrer and the stirrer is turned on to obtain a constant rotation speed of 500 rpm, establishing a vortex in the water which measures about 3 cm depth from highest point of water at the beaker edge to lowest point of air at the vortex center. Observe the vortex from above to ensure it is centered in the beaker, and the magnetic stir bar centered at the vortex center.

Obtain a cleansing phase and fill it into a 1 ml syringe without entrapping air. The syringe has a diameter of about 1.9 mm at the tip (e.g., BD 1 ml tuberculin slip tip, Becton, Dickinson and Co., Franklin Lakes, N.J., USA). Inject the cleansing phase in a steady stream onto the top surface of the water near the beaker edge but not touching the beaker edge. The composition should be injected in about 1 second. Begin a timer and allow the composition to stir for 30 seconds.

Turn off the stirrer. Insert the conductivity probe into the water in a location away from any undissolved solids. Allow the measurement to stabilize and take a conductivity reading and record the Conductivity.

Turn the stirrer back on. Restart the timer as the digital readout passes 250 rpm. After an additional 30 seconds elapsed time, turn off the stirrer and measure the conductivity in the same manner as previous. Record the Conductivity.

Turn the stirrer back on. Restart the timer as the digital readout passes 250 rpm. After an additional 60 seconds elapsed time, turn off the stirrer and measure the conductivity in the same manner as previous. Record the Conductivity.

Remove the probe from the water without disturbing any remaining solids. Cap the beaker with a suitable watertight cover, e.g., plastic wrap and a rubber band. Shake the beaker vigorously for about 30 seconds to dissolve remaining solids, using a vortex type agitator in addition if necessary.

Uncap the beaker, measure conductivity and record the value as the Final Conductivity.

The Dissolution % at each time point is calculated according to the following equation:

$$\text{Dissolution \%} = 100\% \times \frac{(\text{Conductivity} - \text{Initial Water Conductivity})}{(\text{Final Conductivity} - \text{Initial Water Conductivity})}$$

Repeat the measurement as needed to obtain a representative average value.

Dissolution testing data on STnS compositions is illustrated in FIG. 1.

At the 60 second time point, compositions of the present invention have a Dissolution % of at least about 60%, alternatively at least about 70%, alternatively at least about 80%. At the 120 second time point, compositions of the present invention have a Dissolution % of at least about 80%, alternatively at least about 85%, alternatively at least about 90%, alternatively at least about 95%.

Third-Phase Method for Determining Structured Surfactant Stability

The "Third-Phase" Method is used to determine structured surfactant phase stability in a personal cleansing composition. The method involves placing the personal care compositions at 50° C. for 10 days for rapid aging. After rapid aging, transfer about 4 grams of the composition into a Beckman Centrifuge Tube (11×60 mm). Place the centrifuge tube in a Beckman LE-80 Ultracentrifuge and operate the Ultracentrifuge under the following conditions: 50,000 rpm, 2 hours, and @40 C.

Figure 10:
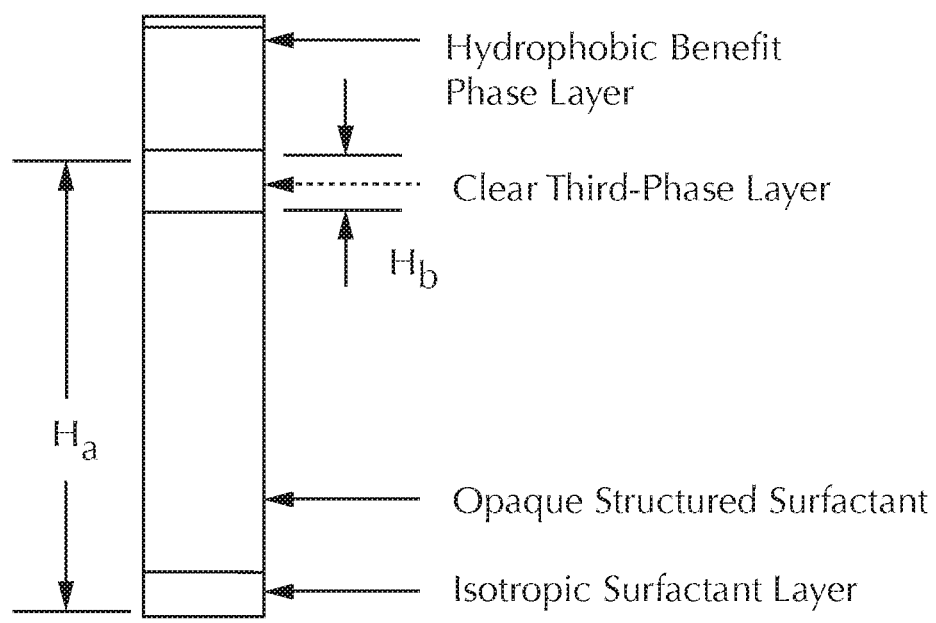
FIG. 10 is an illustration for determining the third-phase volume.

After Ultracentrifugation, determine the third-phase volume by measuring the height of various surfactant phases using an Electronic Digital Caliper (within 0.01 mm) as illustrated in FIG. 10. An example is shown in FIG. 10 for personal cleansing composition comprising Expancel microsphere.

The very top layer is hydrophobic benefit phase layer (hydrocarbons or soybean oil etc.). The layers below the hydrophobic benefit phase layers contain surfactant/water are determined in the following: $H_a$ is the height of all layers containing surfactant/water and $H_b$ is the height of the clear "third-phase" layer just below the hydrophobic benefit phase layer. It is important to record the readings within 30 mins after the Ultracentrifugation is finished to minimize material migration across different layers. The third phase volume is calculated as: Third-phase Volume $\% = H_b/H_a * 100\%$ Preferably, the structured surfactant composition comprises less than 10% "third-phase" volume after rapid aging stability protocol. More preferably, the structured surfactant composition comprises less than 5% "third-phase" volume after rapid aging stability protocol. More preferably, the structured surfactant composition comprises less than 2% "third-phase" volume after rapid aging stability protocol. Even more preferably, the structured surfactant composition comprises less than 1% "third-phase" volume after rapid aging protocol. Most preferably, the structured surfactant composition comprises about 0% "third-phase" volume after rapid aging protocol.

EXAMPLES

The following examples describe and demonstrate embodiments within the scope of the invention. The examples are given solely for the purpose of illustration and are not to be construed as limitations of the present invention, as many variations thereof are possible without departing from the spirit and scope of the invention.

STnS Composition Comparisions

The compositions of Table I (below) were prepared by adding water in a mixing vessel. Then add the following ingredients with continuously mixing: sodium chloride, sodium lauroamphoacetate, sodium trideceth sulfate, sodium tridecyl sulfate, Trideceth-3, EDTA, and sodium benzoate. Adjust pH by adding citric acid solution (50% active) to pH=5.7±0.2. Then, add Methyl chloro isothiazolinone and methyl isothiazolinone. Keep mixing until homogeneous.

Figure 2:
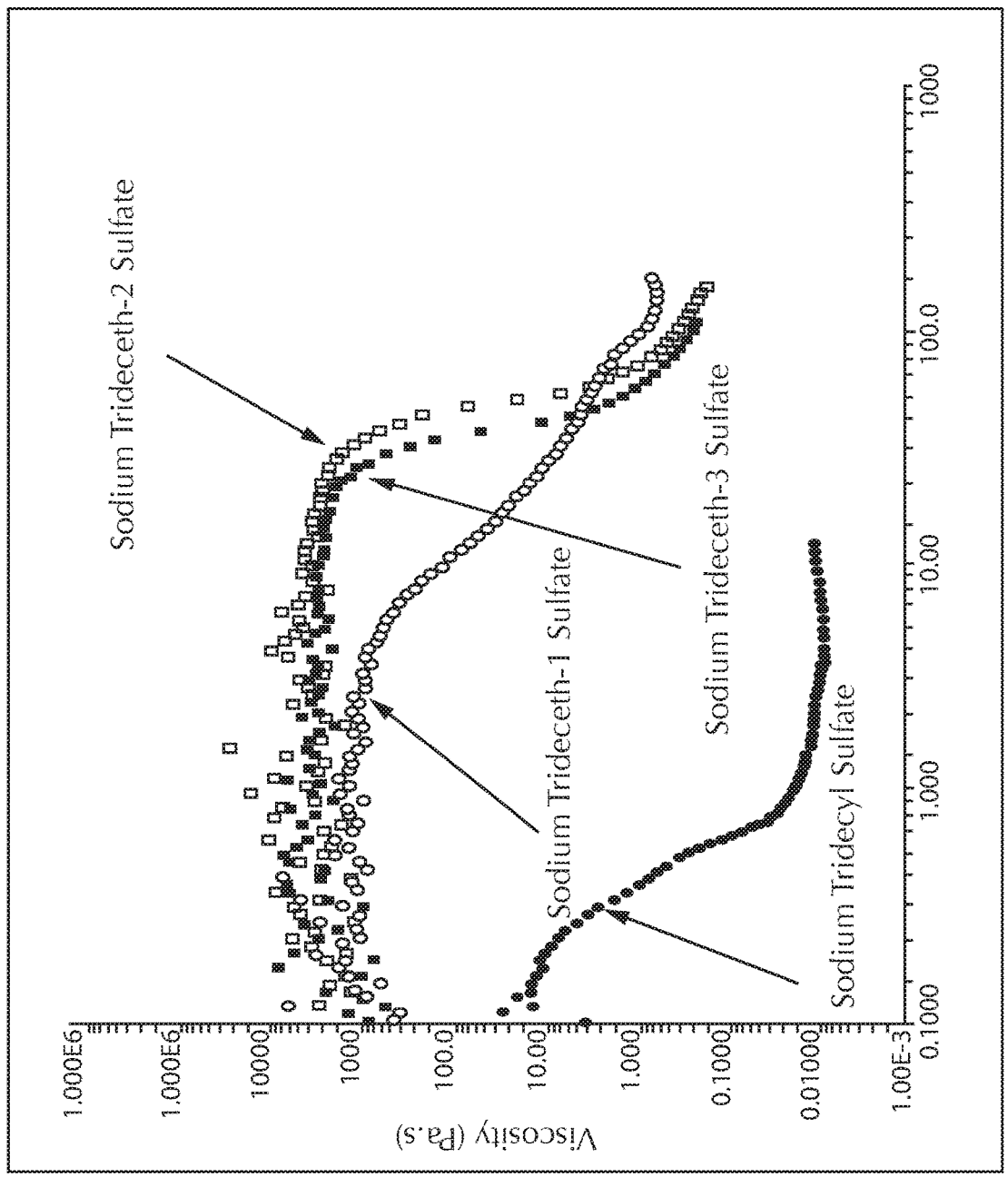
FIG. 2 is a graph of the rheology profile of the STnS series compositions.
Figure 3:
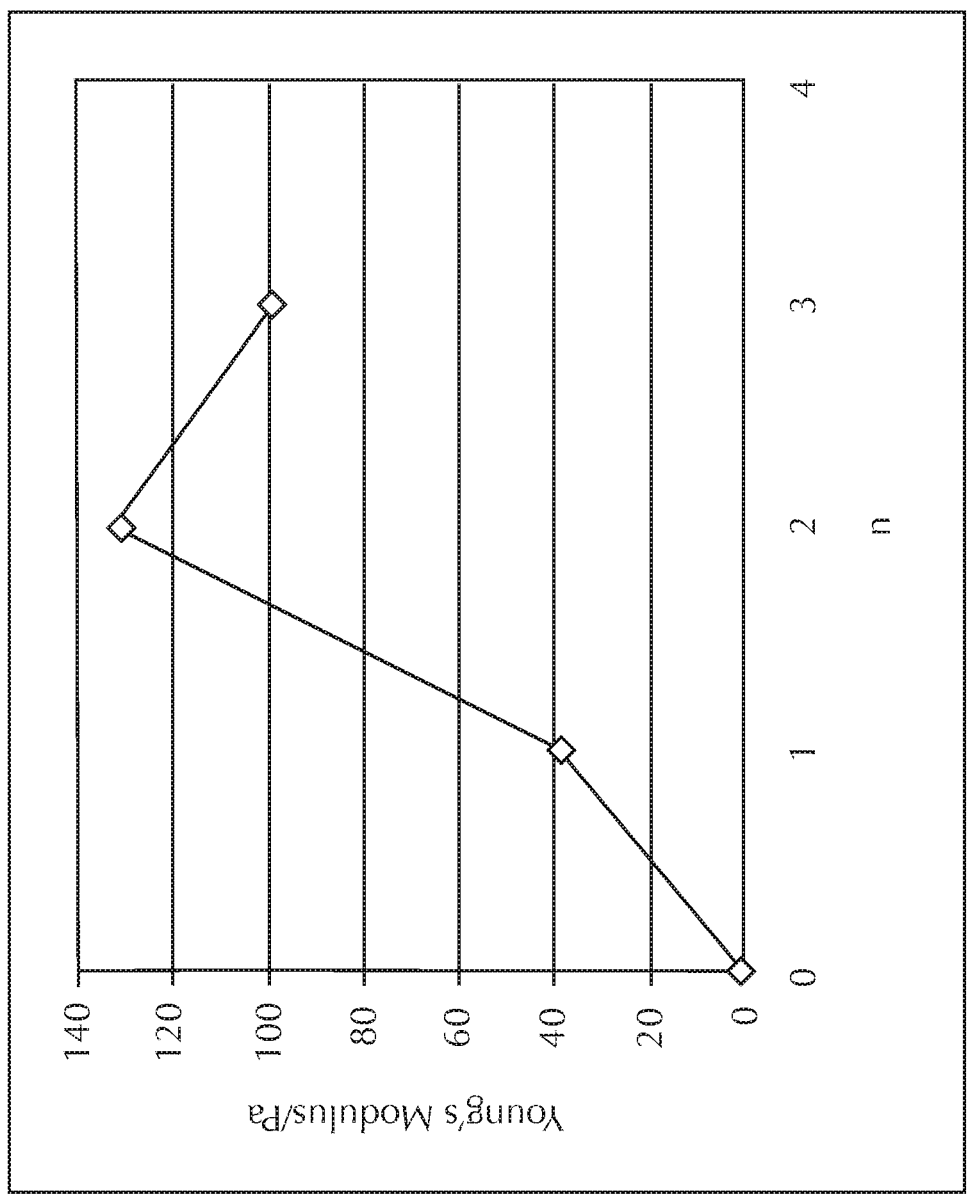
FIG. 3 is a graph of Young's Modulus for the STnS series compositions.

After preparing these compositions, their Lamellar Phase Volume, Young's Modulus, and Zero Shear Viscosity were determined utilizing the methods disclosed herein. The results are captured below in Table I, as well as graphically in FIGS. 2 and 3. FIG. 2 displays the viscosity profile as a function of shear stress of inventive and comparative examples. It is shown that the viscosity profile of inventive Example 2 (labeled as sodium triceth-2 sulfate) is significantly higher than the comparative Example 4 (labeled as Sodium Triceth-1 Sulfate) and comparative Example 3 (labeled as Sodium Tridecyl Sulfate) and is also higher comparative Example 1 (labeled as Sodium Trideceth-3 Sulfate). FIG. 3 graphically depicts the Young's Modulus for the examples in Table I.

Lipid Stability and Lather Performance

The compositions of Table I combined with a second lipid phase, the composition of which is illustrated in Table III(a),

TABLE I

| Surfactant Phase Composition | Comparative Example 1 (w/w %) | Example 2 (w/w %) | Example 3 (w/w %) | Comparative Example 4 (w/w %) |
|---|---|---|---|---|
| Sodium Trideceth-3 Sulfate[1] | 16.56 | — | — | — |
| Sodium Trideceth-2 Sulfate[1] | — | 16.56 | — | — |
| Sodium Trideceth-1 Sulfate[1] | — | — | 16.56 | — |
| Sodium Tridecyl Sulfate[1] | — | — | — | 16.56 |
| Sodium Lauryl Sulfate[2] | | | | |
| Sodium Lauroamphoacetate[3] | 4.94 | 4.94 | 4.94 | 4.94 |
| Trideceth-3 (HLB = 8)[4] | 2.0 | 2.0 | 2.0 | 2.0 |
| Sodium Chloride | 4.75 | 4.75 | 4.75 | 4.75 |
| Methyl chloro isothiazolinone and methyl isothiazolinone[5] | 0.033 | 0.033 | 0.033 | 0.033 |
| EDTA[6] | 0.15 | 0.15 | 0.15 | 0.15 |
| Sodium Benzoate | 0.2 | 0.2 | 0.2 | 0.2 |
| Citric Acid, titrate (pH = ±0.2) | 5.7 | 5.7 | 5.7 | 5.7 |
| Water | Q.S. | Q.S. | Q.S. | Q.S. |
| Total Lathering Surfactant in Cleansing Phase (%) | 21.5% | 21.5% | 21.5% | 21.5% |
| Lamellar Phase Volume (%) | 100% | 100% | 100% | 0% |
| Young's Modulus (Pa) | 100.0 | 131.6 | 38.57 | 0.26 |
| Zero Shear Viscosity (PaS) | 2552 | 3060 | 1029 | 10.7 |

[1]available from Stepan Coporation
[2]available from Procter & Gamble Co.;
[3]available from Cognis Chemical Corp.
[4]Iconal TDA-3 available from BASF Corp.
[5]Kathon CG, available from Rohm & Haas Company, Philadephia, PA;
[6]Dissolvine NA 2x.

Dilution Testing for Examples 1-4

Figure 4:
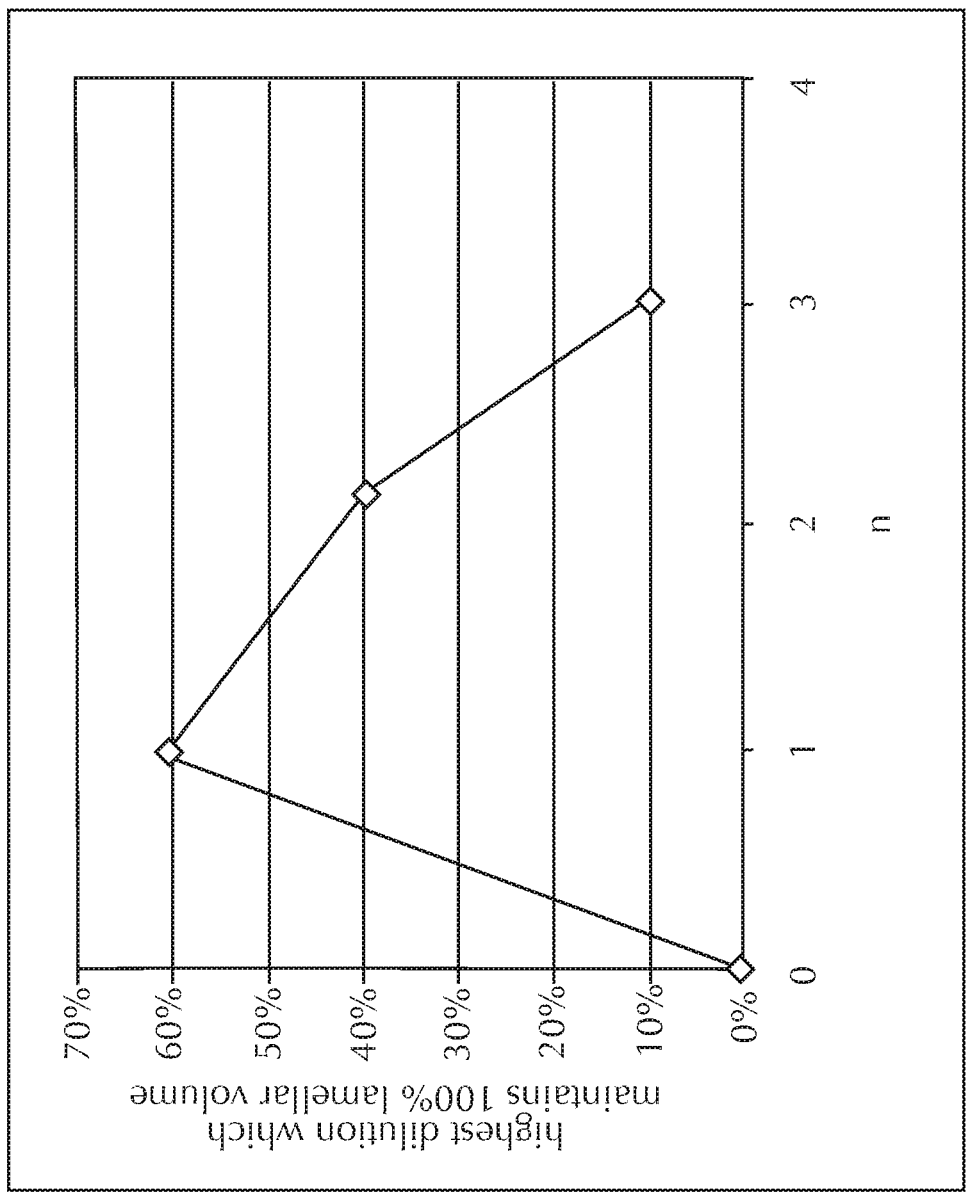
FIG. 4 is a graph capturing the highest dilution maintaining 100% lamellar volume.

The compositions of Table I were tested by diluting in deionozed water. The samples with 10% dilution factors were prepared by adding 10 grams DI water into 90 grams the compositions of comparative and invention examples above. The samples with 20%-60% dilution factors were prepared by adding 20 to 60 grams DI water into 80 to 40 grams the compositions of comparative and invention examples above. These samples were well mixed through a SpeedMixer™ (Model DAC, 400FV available from Fleck-Teck, Inc USA) at 2,000 rpm for 60 seconds. Lamellar phase volume is determined by the Ultracentrifugation method as described in the method section. The results for this test were captured in Table II and graphically represented in FIGS. 4 and 5. FIG. 4 illustrates the highest dilution maintaining a 100% lamellar volume. FIG. 5 illustrates the % lamellar phase as dilution is increased. Inventive Example 2, the ST2S formulation surprisingly maintained a 100% lamellar phase volume up to 40% dilution. The lamellar phase volume of Comparative Example 1 (ST3S) and began decreasing much earlier.

to form a two phase composition. The lipid phase was prepared by heating the petrolatum and mineral to about 88° C. and then mixing petrolatum and mineral oil together. Cool down the lipid phase with agitation until 45° C. Stop agitation and cool the lipid phase overnight to ambient condition. The surfactant and lipid phase are combined through SpeedMixer™ (Model DAC, 400FV available from FleckTeck, Inc USA) at 800 rpm for 60 seconds. After forming these multi-phase compositions, stability testing and later testing are performed. Stability is assessed after aging the products at 50° C. for 10 days. Inventive Example 3 maintained 100% lamellar phase while comparative Example 1 and 2 showed a decreased lamellar phase volume from 100% to about 86% and 77%, respectively. The product lather performance was assessed with a Puff implement. 10 grams of test product are added onto a puff in a circular motion. Add 10 grams of water. Rub products onto puff. Then, hold puff over a beaker to collect lather. Rotate and squeeze puff 10 times, then 10 times in the opposite direction at a speed of one squeeze per second. At the end of rotation, pull the string to squeeze the puff three times.

TABLE II

| Dilution Factor in DI Water | 10% | 20% | 30% | 40% | 50% | 60% |
|---|---|---|---|---|---|---|
| Total Lathering Surfactant Component in Cleansing Phase (%) | 19.35% | 17.2% | 15.05% | 12.9% | 10.75% | 8.6% |
| Lamellar Phase Volume (%) of Comparative Example 1 under Dilution | 100% | 92.07% | 47.44% | 25.77% | 21.84% | 7.27% |
| Lamellar Phase Volume (%) of Example 2 under Dilution | 100% | 100% | 100% | 100% | 69.88% | 32.58% |
| Lamellar Phase Volume (%) of Example 3 under Dilution | 100% | 100% | 100% | 100% | 100% | 100% |
| Lamellar Phase Volume (%) of Comparative Example 4 under Dilution | 0% | 0% | 0% | 0% | 0% | 0% |

Flatten the lather in the beaker and take the volume measurement. The lather volume is rated on the scale as below:

| Observed Lather Volume Range | Rating |
|---|---|
| Lather volume ≤1,000 ml | 1 - Poor |
| 1,000 ml < Lather Volume ≤ 1,500 ml | 2 - Fair |
| 1,500 ml < Lather Volume ≤ 2,000 ml | 3 - Good |
| 2,000 ml < Lather Volume ≤ 2,500 ml | 4 - Very Good |
| Lather volume >2,500 ml | 5 - Excellent |

Inventive Example 3 (Sodium Trideceth-2 Sulfate) showed significantly higher lather volume (2600 ml) than the Comparative Example 4 (Sodium Trideceth-1 Sulfate, 1500 ml). The observed lather volume trend is consistently with the dilution profile shown in FIG. 2. Compositions of Comparative Example 4 (Sodium Trideceth-1 Sulfate) maintained lamellar phase even at high dilution factor (for up to 60% dilution factor) and is therefore slower for lather generation while Inventive Example 3 showed the excellent lamellar phase stability after 10 days @50 C and high lather performance attributing to optimum phase transition at about 40% dilution factor (FIG. 2).

TABLE III(a)

| | Lipid Phase Composition (w/w %) |
|---|---|
| Petrolatum | 70.0 |
| Mineral Oil | 30.0 |

TABLE III(b)

| | Comparative Example 1 + Lipid @55:45 w/w | Inventive Example 2 + Lipid @55:45 w/w | Comparative Example 3 + Lipid @55:45 w/w | Comparative Example 4 + Lipid @55:45 w/w |
|---|---|---|---|---|
| Initial Lamellar Phase Volume | 100% | 100% | 100% | 0% |
| Lamellar Phase Volume after 10 days@50 C. | 77% | 100% | 100% | 0% (not stable) |
| Observed Lather Volume with Puff Implement | 4 Very Good | 5 Excellent | 2 Fair | 5 Excellent |

Comparative Compositions with Cosurfactants

The compositions of Table IV (below) were prepared by were prepared by adding water in a mixing vessel. Then add the following ingredients with continuously mixing: sodium chloride, cocobetaine, cocamidopropyl betaine, lauroamidopropyl betaine, decyl glucoside, sodium cocoyl glycinate, sodium trideceth-2 sulfate, trideceth-3, EDTA, and sodium benzoate. Adjust pH by adding citric acid solution (50% active) to pH=5.7±0.2. Then, add Methyl chloro isothiazolinone and methyl isothiazolinone. Keep mixing until homogeneous.

After preparing these compositions, their Lamellar Phase Volume, Young's Modulus, and Zero Shear Viscosity were determined utilizing the methods disclosed herein. The results are captured below in Table IV. Both comparative and inventive examples have high lamellar phase volumes (70% to 100%), and high Young's Modulus (about 95 Pa to about 249 Pa) and Zero shear viscosities (about 2544 PaS to about 5757 PaS).

TABLE IV

| Surfactant Phase Composition | Exa. 5 (w/w %) | Exa. 6 (w/w %) | Exa. 7 (w/w %) | Comp. Exa. 8 (w/w %) | Comp. Exa. 9 (w/w %) |
|---|---|---|---|---|---|
| Sodium Trideceth-2 Sulfate | 16.56 | 16.56 | 16.56 | 16.56 | 16.56 |
| Cocobetaine | 4.94 | | | | |
| Cocoamidopropyl betaine | | 4.94 | | | |
| Lauroamidopropyl betaine | | | 4.94 | | |
| Decyl Glucoside | | | | 4.94 | |
| Sodium Cocoyl Glycinate | | | | | 4.94 |
| Trideceth-3 (HLB = 8) | 2.0 | 2.0 | 2.0 | 2.0 | 2.0 |
| Sodium Chloride | 4.75 | 4.75 | 4.75 | 4.75 | 4.75 |
| Methyl chloro isothiazolinone and methyl isothiazolinone | 0.033 | 0.033 | 0.033 | 0.033 | 0.033 |
| EDTA | 0.15 | 0.15 | 0.15 | 0.15 | 0.15 |
| Sodium Benzoate | 0.2 | 0.2 | 0.2 | 0.2 | 0.2 |
| Citric Acid, titrate (pH = ±0.2) | 5.7 | 5.7 | 5.7 | 5.7 | 5.7 |
| Water | Q.S. | Q.S. | Q.S. | Q.S. | Q.S. |
| Total Lathering Surfactant Component in Cleansing Phase (%) | 21.5% | 21.5% | 21.5% | 21.5% | 21.5% |
| Lamellar Phase Volume (%) | 100% | 100% | 100% | 70% | 100% |

TABLE IV-continued

| Surfactant Phase Composition | Exa. 5 (w/w %) | Exa. 6 (w/w %) | Exa. 7 (w/w %) | Comp. Exa. 8 (w/w %) | Comp. Exa. 9 (w/w %) |
|---|---|---|---|---|---|
| Young's Modulus (Pa) | 95.1 | 248.9 | 134.2 | 185.5 | 176.6 |
| Zero Shear Viscosity (PaS) | 2544 | 5757 | 3507 | 4809 | 3836 |

Dilution Testing for Examples 5-9

Figure 6:
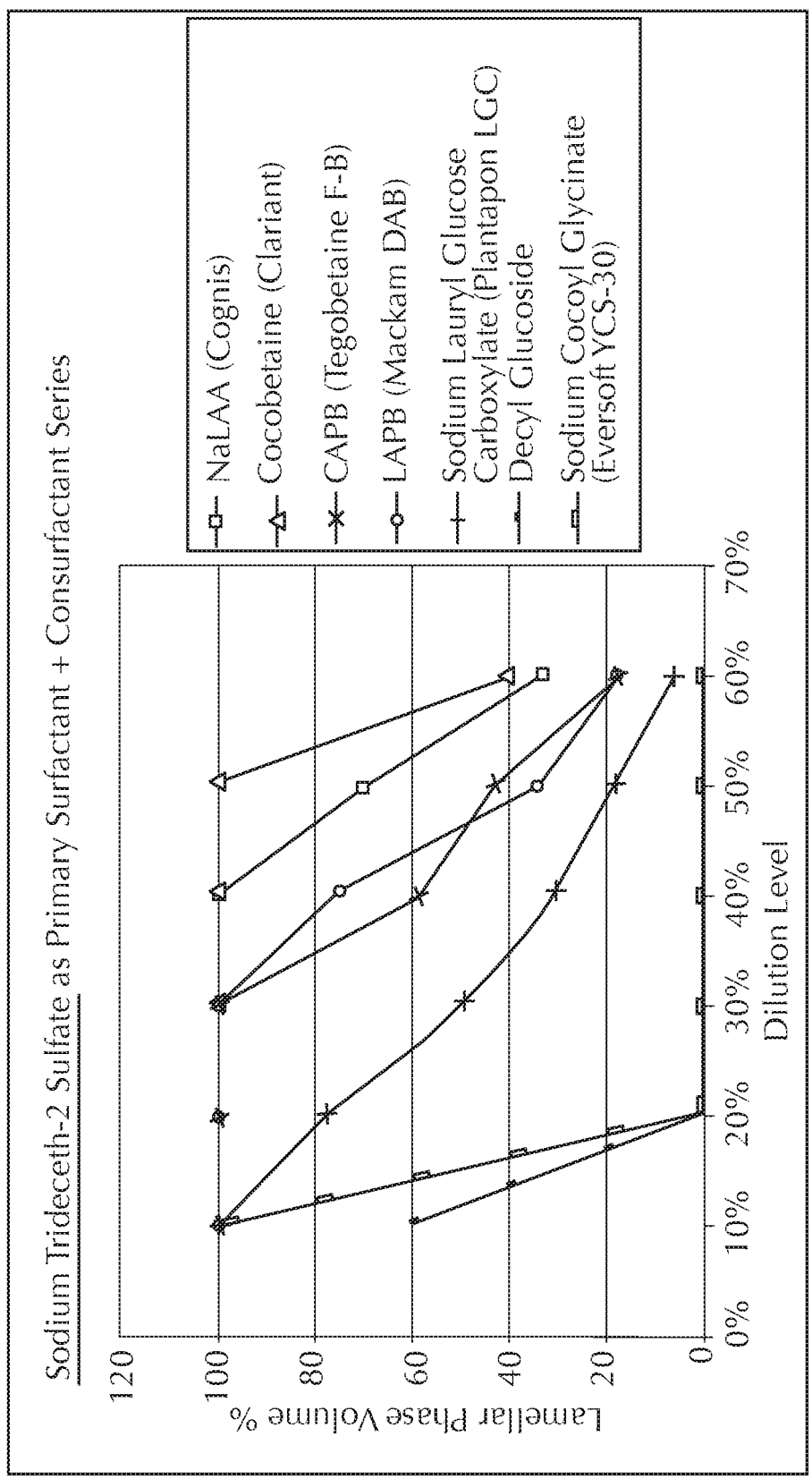
FIG. 6 is a graph of the lamellar phase volume during dilution level of an ST2S composition with differing cosurfactants.

The compositions of Table IV(a) were tested by diluting in deionozed water based on the same procedure described in details under dilution testing for Example 1-5. The results for this test were captured in Table V and graphically represented in FIG. 6. FIG. 6 also contains the dilution profile of inventive Example 3 (sodium lauroamphoacetate). Inventive Examples 5-7 of the ST2S formulation surprisingly maintained a high lamellar phase volume up to 30%-50% dilution. The lamellar phase volume of Comparative Example 8 and 9 began decreasing much earlier (less than 20% dilution factor).

TABLE V

| Dilution Factor in DI Water | 10% | 20% | 30% | 40% | 50% | 60% |
|---|---|---|---|---|---|---|
| Total Lathering Surfactant Component in Cleansing Phase (%) | 19.35% | 17.2% | 15.05% | 12.9% | 10.75% | 8.6% |
| Lamellar Phase Volume (%) of Example 5 under Dilution | 100% | 100% | 100% | 100% | 100% | 37.7% |
| Lamellar Phase Volume (%) of Example 6 under Dilution | 100% | 100% | 100% | 58.6% | 42.4% | 18.3% |
| Lamellar Phase Volume (%) of Example 7 under Dilution | 100% | 100% | 100% | 74.6% | 34.4% | 18.3% |
| Lamellar Phase Volume (%) of Example 8 under Dilution | 61% | 0% | 0% | 0% | 0% | 0% |
| Lamellar Phase Volume (%) of Example 9 under Dilution | 100% | 0% | 0% | 0% | 0% | 0% |

Lipid Stability and Lather Performance

Figure 7:
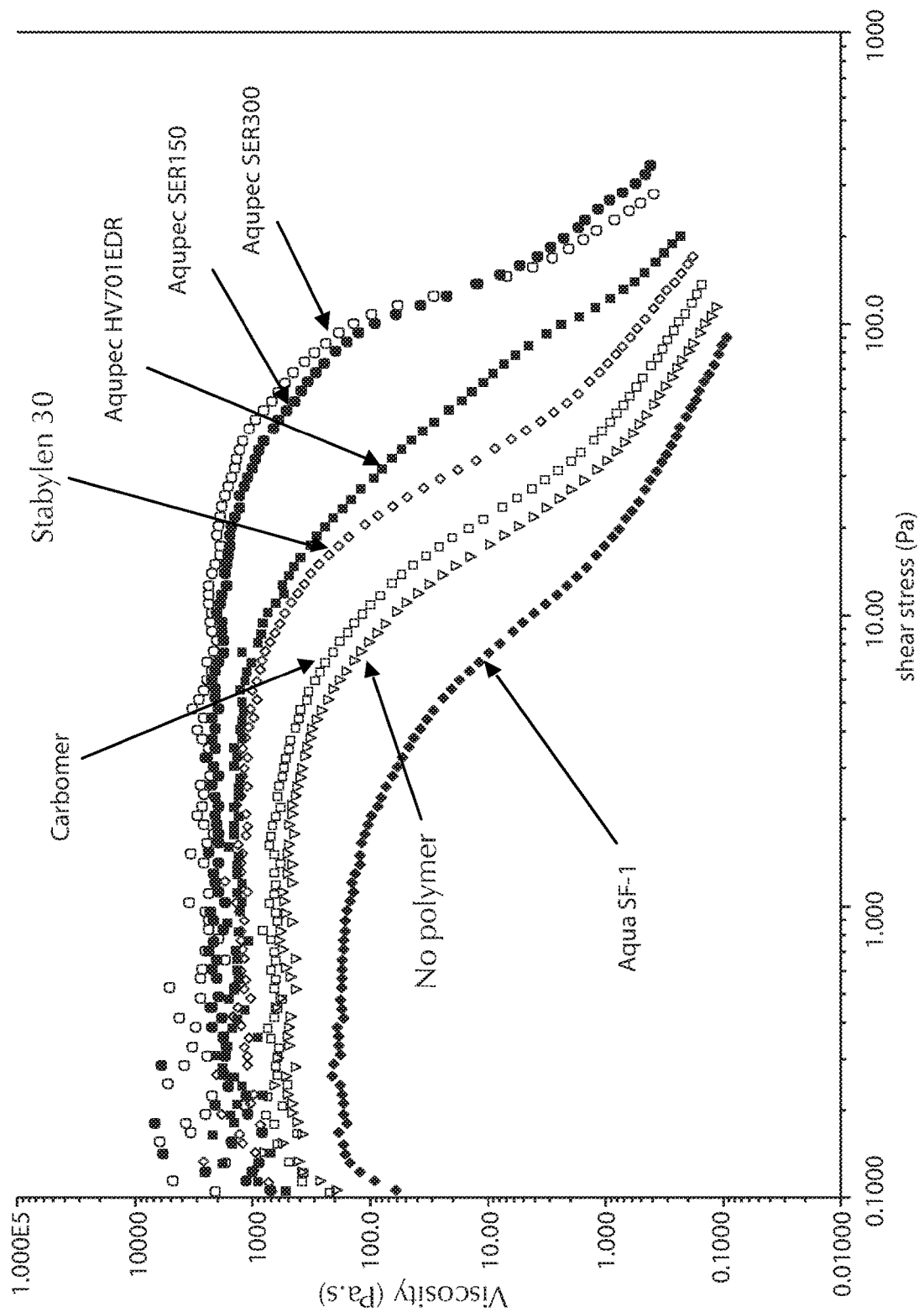
FIG. 7 is a graph of the rheology profile of STnS compositions with differing associative polymers.

The compositions of Table IV combined with a second lipid phase, the composition of which is illustrated in Table III(a), to form a multiphase composition. The surfactant and lipid phase are combined through SpeedMixer™ (Model DAC, 400FV available from FleckTeck, Inc USA) at 800 rpm for 60 seconds. After forming these multi-phase compositions, stability testing and later testing are performed. Stability is assessed by measuring the lamellar phase volume through Ultracentrifugation Method after aging the products at 50° C. for 10 days. Inventive Examples 5-7 maintained 100% lamellar phase while comparative Examples 8-9 showed a decreased lamellar phase volume from 100% to about 0%. The lamellar phase stability profile is showing a surprisingly similar trend as shown the FIG. 7 which showed that Comparative Example 8-9 had a significant decrease in lamellar phase volume at low dilution factors while inventive Example 2, 5-7 showed phase transition points at higher dilution factors.

Comparative Compositions with Associative Polymers

Examples 10-16 illustrate the effectiveness of the associative polymers of the current invention. The compositions of Table VI (below) were prepared by first adding water in a mixing vessel. Then add the following ingredients with continuously mixing: sodium chloride, guar hydroxypropyltrimonium chloride, sodium lauroamphoacetate, sodium trideceth-2 sulfate. Then add the polymer powers (Aqupec and Stabylen 30 polymers) in trideceth-3 to form a premix. Add the polymer-trideceth-3 premix into the main mixing vessel with adequate agitation. Aqua SF-1 is an aqueous dispersion and is added directly into the mixing vessel without premixing with trideceth-3. Then add EDTA and sodium benzoate. Adjust pH by adding citric acid solution (50% active) to pH=5.7±0.2. Then, add Methyl chloro isothiazolinone and methyl isothiazolinone. Keep mixing until homogeneous. The multiphase composition is prepared by adding soybean oil into the surfactant phase composition through a SpeedMixer™ at a speed of 2,000 rpm for 60 seconds.

TABLE VI

| | Exa. 5 + Lipid @55:45 w/w | Exa. 6 + Lipid @55:45 w/w | Exa. 7 + Lipid @55:45 w/w | Comp. Exa. 8 + Lipid @55:45 w/w | Comp. Exa. 9 + Lipid @55:45 w/w |
|---|---|---|---|---|---|
| Initial Lamellar Phase Volume | 100% | 100% | 100% | 69.7% | 100% |
| Lamellar Phase Volume after Stability 10 days@50 C. | 100% | 100% | 100% | 0% (not stable) | 0% (not stable) |

After preparing these compositions, their Lamellar Phase Volume, Young's Modulus, and Zero Shear Viscosity were determined utilizing the methods disclosed herein. The results were captured below in Table VII. Inventive Example 11-14 showed a significant increase in Young's Modulus from about 145% to about 388% while comparative examples 15 and 16 showed minimal to negative effect to the structure of the composition. The magnitude of the Young's modulus increase is surprising due to the low usage level (about 0.2%). It is believed the synergistic behavior is attributed to strong associating interaction between the hydrophobic chain of the polymer and the lamellar vesicles of the surfactant composition.

TABLE VII

| Composition | Comp. Ex. 10 (w/w %) | Ex. 11 (w/w %) | Ex. 12 (w/w %) | Ex. 13 (w/w %) | Ex. 14 (w/w %) | Comp. Ex. 15 (w/w %) | Comp. Ex. 16 (w/w %) |
|---|---|---|---|---|---|---|---|
| Sodium Trideceth-2 Sulfate | 7.30 | 7.30 | 7.30 | 7.30 | 7.30 | 7.30 | 7.30 |
| Sodium Lauroamphoacetate | 2.18 | 2.18 | 2.18 | 2.18 | 2.18 | 2.18 | 2.18 |
| Trideceth-3 (HLB = 8) | 0.88 | 0.88 | 0.88 | 0.88 | 0.88 | 0.88 | 0.88 |
| Sodium Chloride | 4.28 | 4.28 | 4.28 | 4.28 | 4.28 | 4.28 | 4.28 |
| Guar Hydroproyltrimomium Chloride | 0.38 | 0.38 | 0.38 | 0.38 | 0.38 | 0.38 | 0.38 |
| Acrylates/C10-C30 Alkylacrylates crosspolymer (Aqupec SER-300) | | 0.18 | | | | | |
| Acrylates/C10-C30 Alkylacrylates crosspolymer (Aqupec SER-150) | | | 0.18 | | | | |
| Acrylates/C10-C30 Alkylacrylates crosspolymer (Aqupec HV-701EDR) | | | | 0.18 | | | |
| Acrylates/Vinyl isodecanoate crosspolymer (Stabylen 30) | | | | | 0.18 | | |
| Carbomer (Aqupec HV504E) | | | | | | 0.18 | |
| Acrylate copolymer (Aqu SF-1) | | | | | | | 0.18 |
| Methyl chloro isothiazolinone and methyl isothiazolinone[5] | 0.03 | 0.03 | 0.03 | 0.03 | 0.03 | 0.03 | 0.03 |
| EDTA[6] | 0.14 | 0.14 | 0.14 | 0.14 | 0.14 | 0.14 | 0.14 |
| Sodium Benzoate | 0.18 | 0.18 | 0.18 | 0.18 | 0.18 | 0.18 | 0.18 |
| Citric Acid, titrate (pH = ±0.2) | 5.7 | 5.7 | 5.7 | 5.7 | 5.7 | 5.7 | 5.7 |
| Soybean Oil | 10 | 10 | 10 | 10 | 10 | 10 | 10 |
| Water | Q.S. | Q.S. | Q.S. | Q.S. | Q.S. | Q.S. | Q.S. |
| Total Lathering Sulfactant Component in Composition | 9.48% | 9.48% | 9.48% | 9.48% | 9.48% | 9.48% | 9.48% |
| Lamellar Phase Volume (%) | 93% | 96.4% | 100% | 100% | 100% | 87% | 100% |
| Young's Modulus (Pa) | 19.04 | 93.04 | 76.67 | 52.43 | 46.77 | 19.57 | 6.6 |
| Young Modulus Increase % vs. No Polymer Control | — | 388% | 303% | 175% | 145% | 3% | −65% |
| Cylinder Lather Volume (ml) | 530 | 505 | 480 | 482 | 495 | 545 | 520 |

Comparative Compositions with Cationic Deposition Polymers

The compositions of Table VIII (below) were prepared by adding water in a mixing vessel. Then add the following ingredients with continuously mixing: sodium chloride, guar hydroxypropyltrimonium chloride, sodium lauroamphoacetate, sodium trideceth sulfate, Trideceth-3, EDTA, and sodium benzoate. Adjust pH by adding citric acid solution (50% active) to pH=5.7±0.2. Then, add Methyl chloro isothiazolinone and methyl isothiazolinone. Keep mixing until homogeneous. The benefit phase was prepared by heating petrolatum and glyceryl mono-oleate to about 85° C. Then blend Petrolatum and Glyceryl mono-oleate together with mixing. Cool the lipid phase down to 45° C. with slow agitation. Stop agitation and cool the lipid phase to ambient temperature overnight. Add TiO2 to the lipid through a SpeedMixer™ 2,000rpm for 60 seconds. The deposition was assessed by an in-vitro deposition method (Delta-L). The data showed that the charge density of the cationic polymer is critical for deposition. When the cationic charge density is too low (less than 0.8 meq/g) or too high (higher than 2.0 meq/g), the deposition is significantly reduced. The optimum charge density for achieving high deposition is between about 0.8 meq/g to about 2.0 meq/g.

TABLE VIII

|  | Comp. Example 17 | Comp. Example 18 | Example 19 | Example 20 | Example 21 |
|---|---|---|---|---|---|
| I: Surfactant Phase Composition | | | | | |
| Sodium Trideceth-2 Sulfate | 11.59 | 11.59 | 11.59 | 11.59 | 11.59 |
| Sodium Lauroamphoacetate | 3.46 | 3.46 | 3.46 | 3.46 | 3.46 |
| Trideceth-3 (HLB = 8) | 1.40 | 1.40 | 1.40 | 1.40 | 1.40 |
| Sodium Chloride | 4.75 | 4.75 | 4.75 | 4.75 | 4.75 |
| Guar Hydroproyltrimomium Chloride (charge density = 0.18 meq/g) | 0.60 | | | | |
| Guar Hydroproyltrimomium Chloride (charge density = 0.72 meq/g) | | 0.60 | | | |
| Guar Hydroproyltrimomium Chloride (charge density = 0.95 meq/g) | | | 0.60 | | |
| Guar Hydroproyltrimomium Chloride (charge density = 1.60 meq/g) | | | | 0.60 | |
| Guar Hydroproyltrimomium Chloride (charge density = 2.45 meq/g) | | | | | 0.60 |
| (pH = ±0.2, citric acid or NaOH) | (5.7) | (5.7) | (5.7) | (5.7) | (5.7) |
| EDTA | 0.15 | 0.15 | 0.15 | 0.15 | 0.15 |
| Sodium Benzoate | 0.2 | 0.2 | 0.2 | 0.2 | 0.2 |
| Methyl chloro isothiazolinone and methyl isothiazolinone | 0.033 | 0.033 | 0.033 | 0.033 | 0.033 |
| Water | Q.S. | Q.S. | Q.S. | Q.S. | Q.S. |
| II: Benefit Phase Composition | | | | | |
| Petrolatum | 91.47 | 91.47 | 91.47 | 91.47 | 91.47 |
| Glyceryl mono-oleate | 1.87 | 1.87 | 1.87 | 1.87 | 1.87 |
| titanium oxide (RBTD-834-11S2 from Kobo Products) | 6.66 | 6.66 | 6.66 | 6.66 | 6.66 |
| III: Surfactant Phase to Benefit Phase Ratio (w/w) | 85:15 | 85:15 | 85:15 | 85:15 | 85:15 |
| In-vitro Deposition (Delta L) | 0.36 | 7.65 | 16.96 | 18.70 | 8.75 |

Additional Exemplary Formulations

Additional exemplary formulations are listed below in Table IX below.

TABLE IX

| Compositions | Ex. 22 (w/w %) | Ex. 23 (w/w %) | Ex. 24 (w/w %) | Ex. 25 (w/w %) | Ex. 26 (w/w %) | Ex. 27 (w/w %) | Ex. 28 (w/w %) | Ex. 29 (w/w %) |
|---|---|---|---|---|---|---|---|---|
| Sodium Trideceth-2 Sulfate | 7.30 | 7.30 | 7.30 | 6.89 | 10.3 | 6.5 | 6.5 | 7.30 |
| Sodium lauroamphoacetate | 2.18 | 2.18 | 2.18 | 2.05 | — | 1.9 | 1.9 | — |
| Cocamidopropyl betaine | — | — | — | — | 3.18 | — | — | 2.18 |
| Trideceth-3 | 0.88 | 0.88 | 0.88 | 0.83 | 1.24 | 0.78 | 0.78 | 0.88 |
| Guar hydroxypropyltrimonium chloride (N-Hance 3196, CD = 0.7 meq/g) | — | — | — | — | 0.53 | — | — | — |
| Guar Hydroxypropyltrimonium chloride (N-Hance CG-17, CD = 0.9 meq/g) | 0.38 | 0.38 | 0.38 | 0.36 | — | 0.34 | 0.34 | 0.38 |
| Acrylates/C10-C30 alkylacrylates cross polymer (Aqupec SER 300) | 0.18 | 0.18 | 0.18 | 0.17 | — | 0.16 | 0.16 | 0.18 |
| PEG-90M | — | — | — | — | 0.13 | — | — | — |
| Sodium Chloride | 4.28 | 4.28 | 4.28 | 4.04 | 4.22 | 4.5 | 4.5 | 4.28 |
| Citric acid/sodium hydroxide | pH = 5.7 | pH = 5.7 | pH = 5.7 | pH = 5.7 | pH = 5.7 | pH = 5.7 | pH = 5.7 | pH = 5.7 |
| Petrolatum | 9.80 | — | 1.96 | — | — | — | — | — |
| Glyceryl monooleate | 0.20 | — | .04 | — | — | — | — | — |
| Soybean oil | — | 10.0 | 8 | 15.0 | 10 | — | 5.0 | 10.0 |
| Dimethicone | — | — | — | — | — | 5.0 | — | — |
| Water/preservatives/perfume | Q.S. | Q.S. | Q.S. | Q.S. | Q.S. | Q.S. | Q.S. | Q.S. |
| Lamellar Phase % | | | | | | | | |
| Young's Modulus (Pa) | 114.2 | 47.6 | 33.7 | 18.4 | 36.0 | 28.4 | 33.5 | 43.7 |

Clinical Study: Evaluation of Skin Moisturization Benefit

The clinical study design was a leg controlled application test (LCAT) protocol for body wash used to evaluate the beneficial effects of personal care products on dry leg skin. Leg wash studies are designed to approximate consumer-relevant exposure levels, e.g. washing frequency. The technique used in this study is a modification of a published procedure (Ertel, et al, 1999). References: Ertel, K. D., Neumann, P. B., Hartwig, P. M., Rains, G. Y., and Keswick, B. H., *Leg Wash protocol to assess the skin moisturization potential of personal cleansing products. Int. J. Cosmet. Sci.* 21: 383-397 (1999)

Clinical design: Human subjects were screened for dry skin score at 2.0 or higher, in accordance with the dryness grading procedure described herein below.

| Grade[a] | Dryness[b] |
|---|---|
| 0.0 | perfect skin |
| 1.0 | patches of checking and/or slight powderiness, occasional patches of small scales may be seen, distribution generalized |
| 2.0 | generalized slight powderiness, early cracking or occasional small lifting scales may be present |
| 3.0 | generalized moderate powderiness and/or moderate cracking and scales |
| 4.0 | generalized heavy powderiness and/or heavy cracking and lifting scales |
| 5.0 | generalized high cracking and lifting scales, eczematous change may be present but not prominent, may see bleeding cracks |
| 6.0 | generalized severe cracking, bleeding cracks and eczematous changes may be present, large scales may be sloughing off |

[a] half-unit grades may be used if necessary
[b] 'generalized' refers to situations where more than 50% of the application area is affected A cohort of 38 subjects was selected for each treatment. All subjects were pre-conditioned with Olay® soap bar for 7 days followed by 1 application/day for 3 weeks and 2 day regression. Measurements included dry skin grade, corneometer, TEWL, cutometer, and tape strips to obtain biomarker analytes. The treatment design is shown in TABLE X below. Code A was a no treatment control (water only). Code B was a commercial Olay Crème Ribbons Body Wash purchased from Walmart as comparative Example which contains about 25% petrolatum/mineral oil as benefit phase. The formulations for code C, D, E, and F are provided in TABLES XI below. The clinical dryness results are provided in TABLES XII to XV.

TABLE X

LCAT-1 Clinical Design
LCAT-1 Clinical Design

[A] Water (no treatment) (comparative)
[B] Olay Creme Ribbons (comparative, 25% lipid phase)
[C] Inventive Example 30
[D] Inventive Example 31
[E] Inventive Example 32
[F] Inventive Example 33

TABLE XI

| Compositions | Example 30 | Example 31 | Example 32 | Example 33 |
|---|---|---|---|---|
| Sodium Trideceth-2 Sulfate | 6.89 | 7.30 | 6.89 | 6.89 |
| Sodium lauroamphoacetate | 2.05 | 2.18 | 2.05 | — |
| Cocamidopropyl betaine | — | — | — | 2.05 |
| Trideceth-3 | 0.83 | 0.88 | 0.83 | 0.83 |
| Guar Hydroxypropyltrimonium chloride (N-Hance CG-17, CD = 0.9 meq/g) | 0.36 | 0.38 | 0.36 | 0.36 |
| Acrylates/C10-C30 alkylacrylates cross polymer (Aqupec SER 300) | 0.17 | 0.18 | 0.17 | 0.17 |
| Sodium Chloride | 4.04 | 4.28 | 4.04 | 4.04 |
| Citric acid/sodium hydroxide | pH = 5.7 | pH = 5.7 | pH = 5.7 | pH = 5.7 |
| Petrolatum | 14.7 | 9.80 | — | 14.7 |
| Glyceryl monooleate | 0.3 | 0.20 | — | 0.3 |
| Soybean oil | — | — | 15.0 | — |
| Water/preservatives/perfume | Q.S. | Q.S. | Q.S. | Q.S. |
| Total Lathering Surfactant | 8.89 | 9.48 | 8.94 | 8.94 |
| Lamellar Phase Volume % | | | | |
| Young's Modulus (Pa) | | | | |
| Zero shear viscosity (PaS) | | | | |

TABLE XII

Visual dryness results

| Attribute | Evaluation | Sample Size | Treatment | Grouping* | Adjusted Mean | Standard Error |
|---|---|---|---|---|---|---|
| Expert Dryness Grades | Baseline | 37 | [F] Example 33 | a | 2.669 | 0.069 |
| | | 38 | [E] Example 32 | ab | 2.718 | 0.069 |
| | | 38 | [A] Water (no treatment) | ab | 2.749 | 0.069 |
| | | 36 | [B] Olay Crème Ribbons | b | 2.794 | 0.070 |
| | | 37 | [C] Example 30 | b | 2.801 | 0.069 |
| | | 37 | [D] Example 31 | b | 2.824 | 0.069 |
| Expert Dryness Grades | 3 Hrs Post Trt 1 (1.3) | 36 | [C] Example 30 | a | 1.772 | 0.118 |
| | | 37 | [F] Example 33 | a | 1.830 | 0.117 |
| | | 37 | [E] Example 32 | ab | 1.950 | 0.117 |
| | | 35 | [D] Example 31 | ab | 2.022 | 0.120 |
| | | 35 | [B] Olay Crème Ribbons | b | 2.116 | 0.120 |
| | | 36 | [A] Water (no treatment) | c | 2.774 | 0.118 |

TABLE XII-continued

Visual dryness results

| Attribute | Evaluation | Sample Size | Treatment | Grouping* | Adjusted Mean | Standard Error |
|---|---|---|---|---|---|---|
| Expert Dryness Grades | 3 Hrs Post Trt 5 (5.3) | 35 | [C] Example 30 | a | 0.525 | 0.118 |
| | | 36 | [F] Example 33 | a | 0.675 | 0.117 |
| | | 35 | [D] Example 31 | b | 1.089 | 0.118 |
| | | 37 | [E] Example 32 | b | 1.289 | 0.115 |
| | | 34 | [B] Olay Crème Ribbons | b | 1.386 | 0.120 |
| | | 35 | [A] Water (no treatment) | c | 2.828 | 0.118 |
| Expert Dryness Grades | 3 Hrs Post Trt 12 (12.3) | 35 | [C] Example 30 | a | 0.103 | 0.085 |
| | | 36 | [F] Example 33 | ab | 0.129 | 0.084 |
| | | 35 | [D] Example 32 | b | 0.339 | 0.085 |
| | | 34 | [B] Olay Crème Ribbons | c | 0.753 | 0.086 |
| | | 37 | [E] Example 32 | c | 0.927 | 0.083 |
| | | 35 | [A] Water (no treatment) | d | 2.569 | 0.085 |

TABLE XIII

LCAT-2 Clinical Design with Comparative Example 34 and Water.
LCAT-2 Clinical Design
[G] No Treatment - Water Only
[H] Comparative Example 34

| Composition | Comparative Example 34 |
|---|---|
| Sodium Trideceth-3 Sulfate | 6.32% |
| Sodium Lauryl Sulfate | 6.30% |
| Sodium Lauroamphoacetate | 3.74% |
| Sodium Chloride | 4.00% |
| Trideceth-3 | 1.48% |
| Fragrance | 0.80% |
| Citric Acid | 0.70% |
| Guar Hydroxypropyltrimonium Chloride | 0.44% |
| Acrylonitrile/Methacrylonitrile/ Methyl Methacrylate Copolymer, Isopentane | 0.27% |
| Xanthan Gum | 0.16% |
| Sodium Benzoate | 0.15% |
| PEG-90M | 0.11% |
| Disodium EDTA | 0.11% |
| Methylchloroisothiazolinone, Methylisothiazolinone | 0.0004% |
| *Glycine Soja* (Soybean) Oil | 15.0000% |
| Water | Q.S. |

TABLE XIV

Visual Dryness Results of Comparative Example 34

| Attribute | Day | Sample Size | Treatment | Grouping* | Least-Squares Mean | Standard Error |
|---|---|---|---|---|---|---|
| Expert Dryness Grades | Day 1, Baseline | 26 | [H] Comparative Example 34 | ab | 2.615 | 0.077 |
| | | 24 | [G] No Treatment - Water Only | b | 2.744 | 0.080 |
| Expert Dryness Grades | Day 1, 3 Hours | 26 | [H] Comparative Example 34 | a | 2.091 | 0.120 |
| | | 24 | [G] No Treatment - Water Only | b | 2.523 | 0.125 |
| Expert Dryness Grades | Day 5, 3 Hours | 26 | [H] Comparative Example 34 | a | 2.466 | 0.132 |
| | | 24 | [G] No Treatment - Water Only | a | 2.641 | 0.138 |
| Expert Dryness Grades | Day 12, 3 Hours | 24 | [H] No Treatment - Water Only | a | 2.827 | 0.163 |
| | | 26 | [G] Comparative Example 34 | a | 3.137 | 0.156 |

TABLE XV

LCAT-3 Clinical Design with Commercial Body Wash and Water.
LCAT-3 Clinical Design

| Attribute | Evaluation | Sample Size | Treatment | Grouping* | Adjusted Mean | Standard Error |
|---|---|---|---|---|---|---|
| Expert Dryness Grades | Baseline | 47 | [J] Commercial Body Wash Containing Soybean Oil | a | 2.769 | 0.073 |
| | | 46 | [I] No Treatment - Water Only | a | 2.787 | 0.073 |
| Expert Dryness Grades | 3 Hrs Post Trt 1 (1.3) | 46 | [J] Commercial Body Wash Containing Soybean Oil | ab | 2.719 | 0.090 |
| | | 45 | [I] No Treatment - Water Only | b | 2.726 | 0.091 |
| Expert Dryness Grades | 3 Hrs Post Trt 5 (5.3) | 44 | [I] No Treatment - Water Only | a | 3.209 | 0.121 |
| | | 46 | [J] Commercial Body Wash Containing Soybean Oil | a | 3.224 | 0.118 |

[I] No Treatment - Water Only
[J] Commercial Body Wash Containing Soybean Oil

Figure 8:
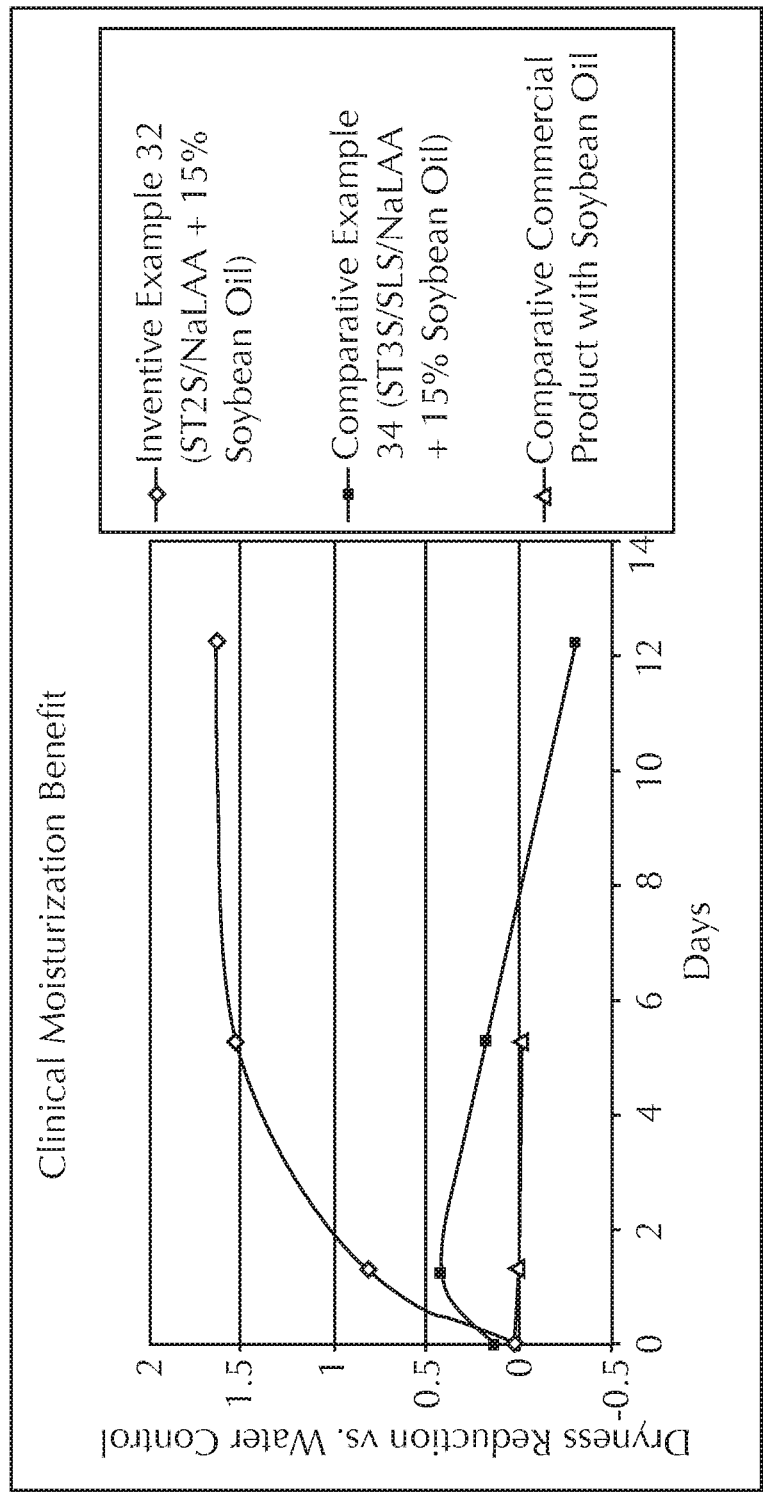
FIG. 8 is a graph of the clinical moisturing benefits.

FIG. 8 shows the clinical moisturization benefits of Inventive Example 32 that contains vs. comparative example 34 and a commercial product that contains soybean oil. It is clear that the inventive Example 32 showed significant skin dryness reduction after 5 days vs. comparative Example 34 and commercial product that contains soybean oil. It is believed there are two may factors that contributed to the significant benefits: one factor is that the inventive examples is essentially free of sodium lauryl sulfate which may have played a negative role causing skin irritation in comparative example 34; and the second key factor is that the inventive example had higher lipid deposition due to the cationic polymer with optimum charge density (0.92 meq/g) vs. comparative example (0.7 meq/g). Both factors are believed to be important for the surprisingly high clinical efficacy for the soybean oil containing compositions.

Exemplary Formulations

It is contemplated that other compositions, such as hand wash, facial cleanser, and hand dish wash, are capable of being formulated with this invention. Exemplary forumlations are listed below.

| Compositions | Ex. 35 (w/w %) | Ex. 36 (w/w %) | Ex. 37 (w/w %) | Ex. 38 (w/w %) | Ex. 39 (w/w %) |
|---|---|---|---|---|---|
| Sodium Trideceth-2 Sulfate | 7.96 | 7.96 | 6.50 | 7.55 | 7.55 |
| Sodium lauroamphoacetate | 2.35 | 2.35 | 1.92 | — | — |
| Cocamidopropyl betaine | — | — | — | 2.23 | 2.23 |
| Trideceth-3 | 0.96 | 0.96 | 0.78 | 0.91 | 0.91 |
| Guar Hydroxypropyltrimonium chloride | 0.41 | 0.41 | 0.34 | 0.30 | — |
| Acrylates/C10-C30 alkylacrylates cross polymer (Aqupec SER 300) | 0.20 | 0.20 | 0.16 | 0.19 | 0.19 |
| Sodium Chloride | 4.66 | 4.66 | 3.80 | 4.42 | 4.22 |
| Citric acid/sodium hydroxide | pH = 5.7 | pH = 5.7 | pH = 5.7 | pH = 5.7 | pH = 5.7 |
| Petrolatum | 1.96 | — | — | — | — |
| Glyceryl monooleate | 0.04 | — | — | — | — |
| Soybean oil | — | 2 | 20 | 7.0 | 10 |
| Water/preservatives/perfume | Q.S. | Q.S. | Q.S. | Q.S. | Q.S. |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising: at least a cleansing phase and a benefit phase wherein: said cleansing phase comprises:

a) an aqueous structured surfactant phase comprising from about 5% to about 20%, by weight of said personal care composition, of STnS where n is between about 0.5 and about 2.7;
b) at least one of the following: an amphoteric surfactant and a zwitterionic surfactant;
c) a structuring system comprising:
   i. optionally, a non-ionic emulsifier;
   ii. optionally, from about 0.05% to about 5%, by weight of said personal care composition, of an associative polymer;
   iii. an electrolyte; and
said benefit phase comprises:
a) from 0.1% to about 50%, by weight of said personal care composition, of a benefit agent;
wherein said personal care composition is free of alkyl sulfate.

2. The personal care composition of claim 1, wherein said personal care composition comprises from about 0.05% to about 0.5%, by weight of said personal care composition, of associative polymer.

3. The personal care composition of claim 2, wherein said associative polymer comprises polyacrylates, hydrophobically modified polysaccharides, hydrophobically modified urethanes, and/or mixtures thereof.

4. The personal care composition of claim 3, wherein said associative polymer comprises an alkyl acrylate polymer.

5. The personal care composition of claim 1, wherein said nonionic emulsifier has an HLB of from about 3.4 to about 8.0.

6. The personal care composition of claim 1, wherein said nonionic emulsifier is selected from the group consisting of glyceryl monohydroxystearate, isosteareth-2, trideceth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

7. The personal care composition of claim 1, wherein the nonionic emulsifier comprises at least one of the following: trideceth-2 and trideceth-3.

8. The personal care composition of claim 1, wherein the electrolyte comprises an anion selected from the group consisting of phosphate, chloride, sulfate, citrate, and mixtures thereof; and a cation selected from the group consisting of sodium, ammonium, potassium, magnesium, and mixtures thereof.

9. The personal care composition of claim 1, wherein said electrolyte is selected from the group consisting of sodium chloride, ammonium chloride, sodium sulfate, ammonium sulfate, and mixtures thereof.

10. The personal care composition of claim 1, wherein said personal care composition comprises from about 0.5 to about 5%, by weight of said personal care composition, of electrolyte.

11. The personal care composition of claim 1, wherein said benefit phase is anhydrous.

12. The personal care composition of claim 1, wherein said benefit agent is selected from the group consisting of petrolatum; lanolin; natural waxes; synthetic waxes; derivatives of lanolin; volatile organosiloxanes; derivatives of volatile organosiloxanes; non-volatile organosiloxanes; derivatives of non-volatile organosiloxanes; lanolin oil; lanolin esters; natural triglycerides; synthetic triglycerides; and combinations thereof.

13. The personal care composition of claim 1 wherein said benefit agent is suitable for use in the present invention and has a Vaughan Solubility Parameter of from about 5 $(cal/cm^3)^{1/2}$ to about 15 $(cal/cm^3)^{1/2}$.

14. The personal care composition of claim 1, wherein said benefit agent is selected from the group consisting of petrolatum, mineral oil, and mixtures thereof.

15. The personal care composition of claim 1, wherein said benefit agent is soybean oil.

16. The personal care composition of claim 1, wherein said benefit phase is substantially free of surfactant.

17. The personal care composition of claim 1, wherein n is between about 1.1 and about 2.5.

18. The personal care composition of claim 1, wherein n is about 2.

19. The personal care composition of claim 1, wherein the aqueous structured surfactant phase comprises from about 5% to about 10% of STnS.

20. The personal care composition of claim 1, wherein the aqueous structured surfactant phase comprises at least a 70% lamellar structure.

* * * * *